(12) United States Patent
Roberts et al.

(10) Patent No.: US 12,686,852 B2
(45) Date of Patent: Jul. 21, 2026

(54) SUPPORT AND SYSTEM FOR ENGINEERED TISSUE

(71) Applicant: Novoheart International Limited, Kowloon (HK)

(72) Inventors: Erin G. Roberts, Kwun Tong (HK); Eugene K. Lee, Kwun Tong (HK); David D. Tran, Kwun Tong (HK); Suet Yee Mak, Kwun Tong (HK); Bernard Fermini, Kwun Tong (HK); Andy Wong, Kwun Tong (HK)

(73) Assignee: Novoheart International Limited, Kowloon (HK)

( * ) Notice: Subject to any disclaimer, the term of this patent is extended or adjusted under 35 U.S.C. 154(b) by 709 days.

(21) Appl. No.: 18/014,897

(22) PCT Filed: Jul. 8, 2021

(86) PCT No.: PCT/US2021/040923
§ 371 (c)(1),
(2) Date: Jan. 6, 2023

(87) PCT Pub. No.: WO2022/011163
PCT Pub. Date: Jan. 13, 2022

(65) Prior Publication Data
US 2023/0257711 A1 Aug. 17, 2023

Related U.S. Application Data

(60) Provisional application No. 63/049,703, filed on Jul. 9, 2020.

(51) Int. Cl.
| | |
|---|---|
| *C12N 5/077* | (2010.01) |
| *C12M 1/12* | (2006.01) |
| *C12M 3/00* | (2006.01) |

(52) U.S. Cl.
CPC .......... *C12N 5/0657* (2013.01); *C12M 21/08* (2013.01); *C12M 25/14* (2013.01);
(Continued)

(58) Field of Classification Search
CPC .............. C12N 5/0657; C12N 2527/00; C12N 2533/00; C12N 2535/00; C12N 2501/155;
(Continued)

(56) References Cited

U.S. PATENT DOCUMENTS

2007/0287763 A1    12/2007  Soucek et al.
2017/0107469 A1*   4/2017   Costa ..................... C12M 23/26
(Continued)

FOREIGN PATENT DOCUMENTS

WO        2022/011163  A1     1/2022

OTHER PUBLICATIONS

Overview of Materiasl for Silicone Rubber (MatWeb Material Property Data, www.matweb.com (Year: 2025).*
(Continued)

*Primary Examiner* — Michael L Hobbs
(74) *Attorney, Agent, or Firm* — K&L Gates LLP; Brian J. Novak; Giorgios N. Kefallinos

(57) ABSTRACT

The present disclosure relates to tissue supports for use with engineered tissues and organoids, such as cardiac organoid chambers. In an embodiment of the present disclosure, the tissue supports are provided with a fluid-impermeable resilient member that is resiliently deformable during testing by cultured tissues formed on the surface of the tissue support.

13 Claims, 22 Drawing Sheets

(52) U.S. Cl.
   CPC ...... *C12N 2527/00* (2013.01); *C12N 2533/00* (2013.01); *C12N 2535/00* (2013.01)

(58) Field of Classification Search
   CPC .......... C12N 2501/727; C12N 2521/00; C12N 2506/45; C12M 21/08; C12M 25/14; C12M 23/20; C12M 35/04
   See application file for complete search history.

(56)                    References Cited

U.S. PATENT DOCUMENTS

2017/0261487 A1    9/2017  Qian et al.
2019/0151509 A1*   5/2019  Kheradvar .......... A61L 27/3826
2019/0365952 A1   12/2019  Singh et al.

OTHER PUBLICATIONS

International Search Report and Written Opinion, mailed Nov. 2, 2021, for International Application Serial No. PCT/US2021/040923 filed on Jul. 8, 2021.

De Clerck et al., "In vivo measurement of QT prolongation dispersion and arrhythmogenesis: application to the preclinical cardiovascular safety pharmacology of a new chemical entity," Blackwell Science Fundamental & Clinical Pharmacology 16 (2002) pp. 125-140.

Milani-Nejad et al., "Small and large animal models in cardiac contraction research: Advantages and disadvantages," Pharmacology & Therapeutics 141 (2014) pp. 235-249.

Magdy et al., "Human Induced Pluripotent Stem Cell (hiPSC)—Derived Cells to Assess Drug Cardiotoxicity: Opportunities and Problems," Annual Review of Pharmacology and Toxicology (2018) pp. 83-103.

Gintant et al., "Evolution of strategies to improve preclinical cardiac safety testing," Nature Reviews | Drug Discovery (2016) pp. 457-471.

Shao et al., "On human pluripotent stem cell control: The rise of 3D bioengineering and mechanobiology," Biomaterials (2015) pp. 26-43.

Wang et al., "Effect of engineered anisotropy on the susceptibility of human pluripotent stem cell-derived ventricular cardiomyocytes to arrhythmias," Biomaterials (2013) pp. 8878-8886.

Laverty et al., "How can we improve our understanding of cardiovascular safely liabilities to develop safer medicines?" British journal of pharmacology (2011) pp. 675-693.

Ferri et al., "Drug attrition during pre-clinical and clinical development: understanding and managing drug-induced cardiotoxicity," Pharmacology & therapeutics (2013) pp. 470-484.

Yin et al., "Engineering stem cell organoids," Cell stem cell (2016) pp. 25-38.

Li et al., "Bioengineering an electro-mechanically functional miniature ventricular heart chamber from human pluripotent stem cells," Biomaterials (2018) pp. 116-127.

Zhang et al., "3D bioprinting for tissue and organ fabrication," Annals of biomedical engineering (2017) pp. 148-163.

Tsuruyama et al., "Pulsatile tubular cardiac tissues fabricated by wrapping human iPS cells-derived cardiomyocyte sheets," Regenerative therapy (2019) pp. 297-305.

Cox et al., "Remodeling and homeostasis of the extracellular matrix: implications for fibrotic diseases and cancer," Disease models & mechanisms (2011) pp. 165-178.

Lee et al., "Fabrication of slender elastic shells by the coating of curved surfaces," Nature communications (2016) pp. 1-7.

Colombo et al., "An analysis of the strain field in biaxial Flexcell membranes for different waveforms and frequencies," Proceedings of the Institution of Mechanical Engineers, Part H: Journal of Engineering in Medicine (2008) pp. 1235-1245.

Pegan et al., "Skin-mountable stretch sensor for wearable health monitoring," Nanoscale (2016) pp. 17295-17303.

Saab, "Applications of high-pressure balloons in the medical device industry," Medical Device & Diagnostic Industry Magazine (2000) pp. 86-94.

Basu et al., "Biodegradable inflatable balloons for tissue separation," Biomaterials (2016) pp. 109-116.

Sun et al., "Novel biodegradable electrospun nanofibrous P(DLLA-CL) balloons for the treatment of vertebral compression fractures," Nanomedicine: Nanotechnology, Biology and Medicine (2013) pp. 829-838.

Byrne et al., "Coronary balloon angioplasty, stents, and scaffolds," The Lancet (2017) pp. 781-792.

Scheller et al., "Treatment of coronary in-stent restenosis with a paclitaxel-coated balloon catheter," New England journal of medicine (2006) pp. 2113-2124.

Lee et al., "Linear Micro-patterned Drug Eluting Balloon (LMDEB) for Enhanced Endovascular Drug Delivery," Scientific reports (2018) pp. 1-13.

Oberhoff et al., "Inhibition of smooth muscle cell proliferation after local drug delivery of the antimitotic drug paclitaxel using a porous balloon catheter," Basic research in cardiology (2001) pp. 275-282.

Stampfl et al., "Langendorff heart: a model system to study cardiovascular effects of engineered nanoparticles," ACS nano (2011) pp. 5345-5353.

Su et al., "Mechanics of stretchable electronics on balloon catheter under extreme deformation," International Journal of Solids and Structures (2014) pp. 1555-1561.

Wang et al., "Fabrication and characterization of a parylene-based three-dimensional microelectrode array for use in retinal prosthesis," Journal of Microelectromechanical Systems (2010) pp. 367-374.

Pakazad et al., "A novel stretchable micro-electrode array (SMEA) design for directional stretching of cells," Journal of Micromechanics and Microengineering (2014) p. 1-10.

Jepsen et al., "Characterization of thin gelatin hydrogel membranes with balloon properties for dynamic tissue engineering," Biopolymers (2019) pp. 1-8.

Keung, Wendy, et al. "Human cardiac ventricular-like organoid chambers and tissue strips from pluripotent stem cells as a two-tiered assay for inotropic responses." Clinical Pharmacology & Therapeutics 106.2 (2019): 402-414.

Roberts, Erin G., et al. "Ultra-Compliant Indwelling Elastomer Balloons Improve Stability and Performance of Bioengineered Human Mini-Hearts." Advanced Engineering Materials 24.8 (2022): 2101481.

Lee, Eun Jung, et al. "Engineered cardiac organoid chambers: toward a functional biological model ventricle." Tissue Engineering Part A 14.2 (2008): 215-225.

* cited by examiner

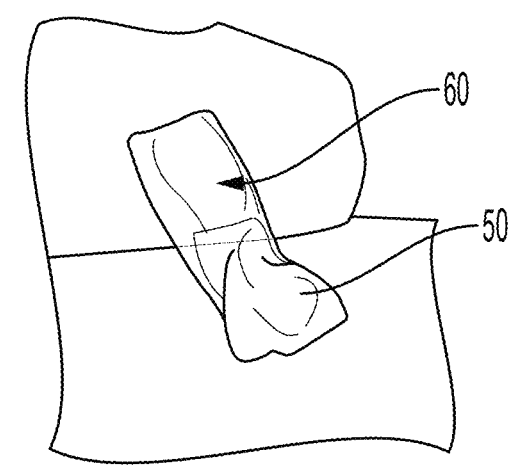
| Tissue type | Approximate elastic modulus |
|---|---|
| Neural | 100 Pa |
| Lung | 200 Pa |
| Smooth Muscle | 5 kPa |
| Cartilage | 15 kPa |
| Bone | 3 GPa |
Fig. 3
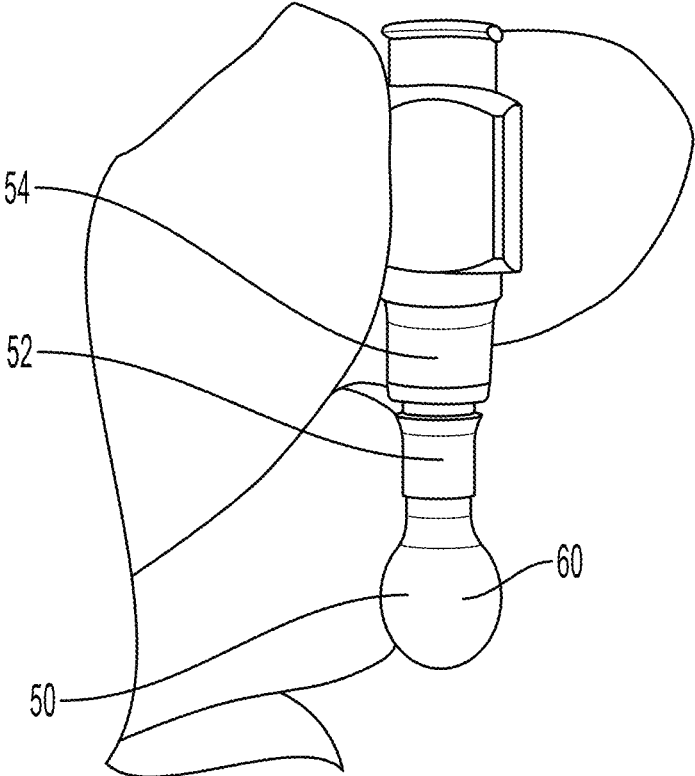
Fig. 4A
Fig. 4B

Normalized Developed Pressure - Injection loading

Normalized Stroke Area - Injection loading

Normalized stroke work - Injection loading

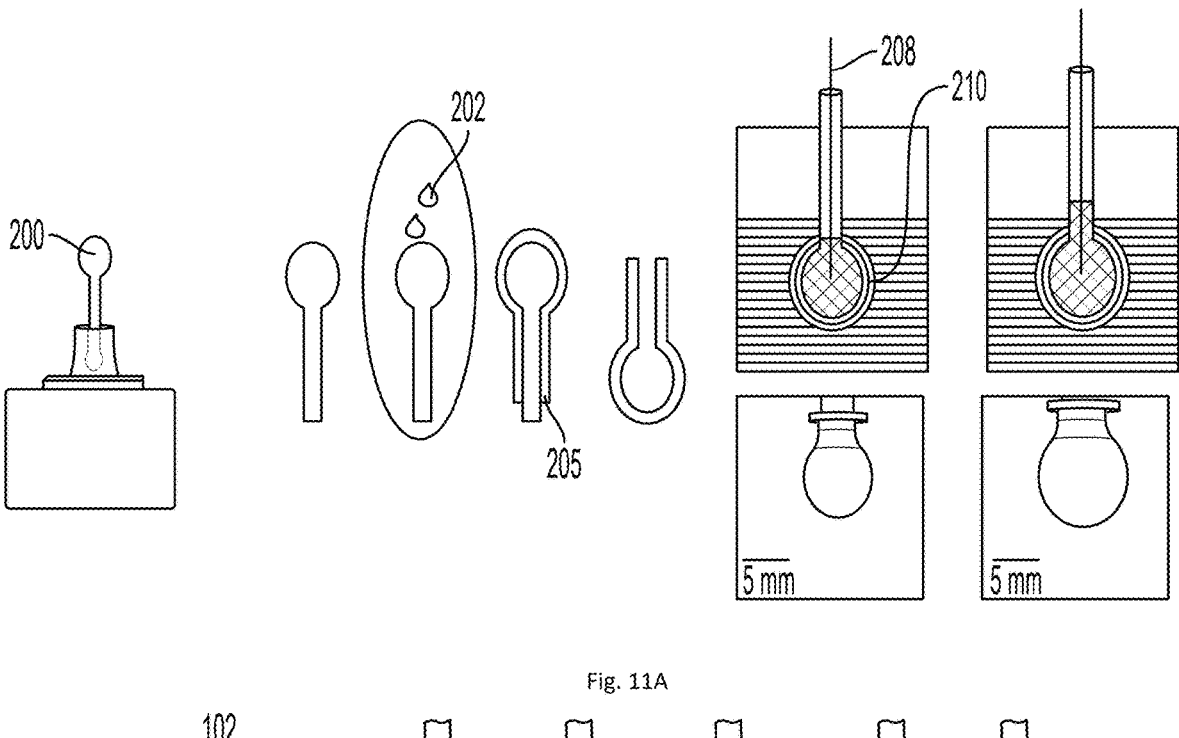
Fig. 11A
Fig. 11B
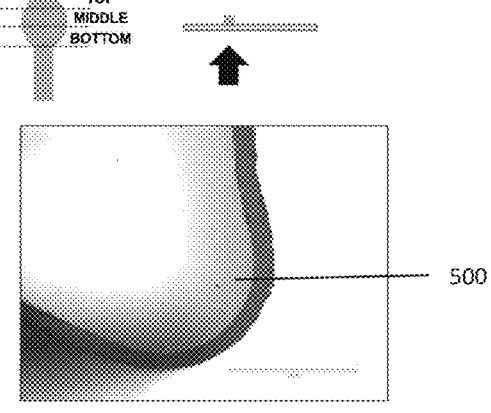
Fig. 12A

SUPPORT AND SYSTEM FOR ENGINEERED TISSUE

CROSS REFERENCE TO RELATED APPLICATIONS

The present application is a national phase filing of PCT/US2021/040923, filed on Jul. 8, 2021, which claims the benefit of U.S. Provisional patent application 63/049,703 filed Jul. 9, 2020, the entire contents of each of which is are incorporated herein by reference.

FIELD

The present disclosure relates to tissue supports for use with engineered tissues and organoids.

BACKGROUND

The pharmaceutical industry currently relies greatly on in vivo animal models to define the safety and efficacy of new drugs. However, animal testing is expensive, resource-intensive, subject to interspecies differences in response, and often fails to predict human outcome because of physiological differences between animals and humans. As a result, engineered human tissue preparations have recently gained importance as models to address issues of translation from preclinical data to clinical outcome [1, 2]. Engineered models of human organ systems can be fabricated using a variety of different cell types, including stem cells derived from human donors; these engineered tissues are used in studies related to drug discovery and development, disease modelling, and implantable tissue replacements.

However, gaining meaningful insights from engineered models relies greatly on having consistency and reproducibility across the fabricated tissues, and current approaches are not deprived of limitations. Protocols for advancing the maturation of cells and tissues differentiated from stem cells are still evolving, and a lack of consistency in cell production and model fabrication all delay progress in the field [3-6]. Consequently, there is a pressing need for the development of methods and techniques that will define best practice, leading to improved consistency and reproducibility in the fabrication, use, and physiological relevance of these engineered tissue models. This, in turn, will greatly improve the value and impact of using engineered tissue constructs to predict clinical outcome.

Cardiovascular toxicity accounts for approximately 40% of all drugs withdrawn from the market due to safety concerns [7,8]. Therefore, there exists particular interest in the fabrication of engineered cardiac organoid chambers, which are useful models for drug safety testing. An organoid is defined as 'an artificially grown mass of cells or tissue that resembles an organ' and often has a more complex structure than a traditional 2D sheet of cells or even a 3D strip of engineered tissue [9]. The fabrication of an organoid chamber and measurements using this tissue construct require certain specific criteria associated with the properties of a contracting hollow chamber.

In preparing cardiac organoids, it is preferable to form a 3D chamber to mimic the physiology and biomechanical properties of the cardiac ventricle and allow for the measurement of a number of clinical endpoints including pressure-volume (PV) data. Chambers can be formed by a number of techniques, including the compaction of a cell and matrix protein solution around a mold, 3D printing of a similar solution in the desired shape, and the wrapping of stacked cellular sheets to create an internal cavity [10-12]. However, there are complications in forming chambers with regards to uniformity and mechanical integrity. Non-uniform, thin-walled chambers often have leaks that diminish their pumping performance, and impair the ability to collect accurate data across a set of chambers.

Inflatable balloon catheters for surgical and drug delivery applications have previously been used as a temporary support upon which a stem cell-derived cardiac organoid chamber is formed as described in US2017/0107469 to Costa et al. As taught in this disclosure, a commercially available balloon catheter is modified by cutting off and sealing the protruding catheter tip. The balloon is then inflated with fluid to a required size, and tissue formed thereon. However, such modified commercially available balloon catheters are not designed to assume a uniform balloon shape upon inflation, leading to geometric variability. Such variability can negatively impact the uniformity of the resulting tissue formed around the balloon, and the eventual pumping performance of the organoid. Further, as the inflated balloon catheter is much too stiff in relation to the forces exerted by the tissue supported on the catheter, it is necessary to remove the balloon from the tissue after tissue compaction around the balloon catheter and in preparation for measurement.

Unfortunately, the resulting tissue is also relatively fragile and often has small breaches in the structure, resulting in "leaky" permeable tissues which have unpredictable results when used for testing purposes. Especially in collection of cardiac data, it is important to be able to measure the changes in pressure and volume as the tissue contracts with each heartbeat; and leaking chambers generate inconsistent data which is poorly representative of the PV relationship of a given cardiac contraction. In addition, the stretching of cardiac organoid chambers by the addition of internal pressure, for example, by applying a hydrostatic load, is a common step during measurement. As loads cannot be applied accurately or consistently across leaking tissues, and cannot be uniformly maintained during testing, any data analysis and interpretation of results obtained is compromised. Removal of deflated catheter also risks tissue damage.

It is an object of the present disclosure to provide a method of preparing tissues and/or organoids such that the resulting tissues and/organoids can provide consistent results and may be used for drug testing platforms.

It is another object of the present disclosure to provide a tissue support and method of fabrication of organoids thereon which addresses or at least ameliorates the above disadvantages or deficiencies, or provides the public with a useful choice.

SUMMARY

Features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims.

In accordance with a first aspect of the present disclosure, there is provided a tissue support comprising a fluid-impermeable resilient member having an external surface and defining an enclosed volume; wherein said external surface of the member is resiliently deformable by cultured tissues formed on the external surface of the member during testing thereof.

In some embodiments, the cultured tissues comprise cardiac cells, which are optionally human ventricular-like cardiomyocytes derived from human pluripotent stem cells. In some embodiments, the cultured tissues are cardiac organoids. In some embodiments, the cultured tissues are advantageously human cardiac ventricular-like organoid chambers.

In some embodiments, the testing is selected from the group consisting of a pressure-volume loop analysis, mechanical stretch measurement, electrophysiological measurement, gene expression analysis at a transcript level, gene expression analysis at a protein level, microstructural analysis using optical microscopy, and microstructural analysis using electron microscopy. In some embodiments, the electrophysiological measurements including conduction velocity, action potential duration, or conduction pattern.

In some embodiments, the testing is a pressure-volume loop analysis, or the testing is performed to study the Frank-Starling mechanism of the cultured tissues. Optionally, the testing is performed in the presence of an electric field proximate the support.

In some embodiments, the cultured tissues are stretched for testing by increasing hydrostatic loading of the enclosed volume. In some embodiments, the resilient deformation of the external surface of the member into the enclosed volume causes a measurable change in the cross sectional area and enclosed volume of the member.

In some embodiments, the fluid-impermeable member defines a substantially spherical enclosed volume in an inflated state, and/or the fluid-impermeable member is formed as a generally spherical balloon in an inflated state. In some embodiments, the inflation of the fluid-impermeable member allows the enclosed volume to assume a predetermined size and shape.

Optionally, the fluid-impermeable member has a wall of generally consistent thickness, said thickness between a thickness of 40-300 μm, more preferably 40-120 μm, more preferably 40-60 μm.

In some embodiments, the fluid-impermeable member further comprises an elongate support portion attachable to a fluid loading port. In some embodiments, the cross sectional area of the fluid-impermeable member advantageously increases generally linearly relative to loading volume of solutions between a range of 300 to 600 μL into the enclosed volume.

In some embodiments, the fluid-impermeable member is formed by a polymeric material with elastic modulus of 1 kPa-10 MPa, 20 kPa-200 kPa, or 60 kPa; in some embodiments, the polymeric material is selected from polydimethylsiloxane, EcoFlex, and NuSil polymers.

In some embodiments, the relative stiffness of the fluid resilient member is advantageously at least one order of magnitude less than the relative stiffness of the tissue supported thereon.

Optionally, the external surface of the fluid resilient member is provided with one or more topological features to guide biophysical interaction between the tissue and the tissue support. In some embodiments, the topological features are advantageously one or more of the group of topological features comprising grooves, ridges, channels, bumps, knobs, dimples, holes, pillars, and other protrusions with both rough and smooth finishes.

Optionally, the external surface is provided with patterned electrodes, or a stretch sensor.

In some embodiments, the fluid-impermeable member is formed by drop casting of a polymeric material on a 3D printed mold.

In accordance with a second aspect of the present disclosure, there is provided a system for observing properties of cultured tissue during testing analysis thereof, the system comprising a fluid-impermeable resilient member having an external surface and defining an enclosed volume; and a cultured tissue construct extending about the fluid-impermeable member and supported thereon; wherein said external surface of the member is resiliently deformable by the tissue constructs during testing thereof.

In some embodiments, the cultured tissues comprise cardiac cells, which are optionally human ventricular-like cardiomyocytes derived from human pluripotent stem cells. In some embodiments, the cultured tissues are cardiac organoids. In some embodiments, the cultured tissues are advantageously human cardiac ventricular-like organoid chambers.

In some embodiments, the testing is selected from the group consisting of a pressure-volume loop analysis, mechanical stretch measurement, electrophysiological measurement, gene expression analysis at a transcript level, gene expression analysis at a protein level, microstructural analysis using optical microscopy, and microstructural analysis using electron microscopy. In some embodiments, the electrophysiological measurements including conduction velocity, action potential duration, or conduction pattern.

In some embodiments, the testing is a pressure-volume loop analysis, or the testing is performed to study the Frank-Starling mechanism of the cultured tissues. Optionally, the testing is performed in the presence of an electric field proximate the support.

In some embodiments, the cultured tissues are stretched for testing by increasing a hydrostatic loading in the enclosed volume, stretching the cardiac tissue. In some embodiments, the resilient deformation of the external surface of the member into the enclosed volume causes a measurable change in the cross sectional area and enclosed volume of the member.

In some embodiments, the fluid-impermeable member defines a substantially spherical enclosed volume in an inflated state, and/or the fluid-impermeable member is formed as a generally spherical balloon in an inflated state. In some embodiments, the inflation of the fluid-impermeable member allows the enclosed volume to assume a predetermined size and shape.

Optionally, the fluid-impermeable member has a wall of generally consistent thickness, said thickness between a thickness of 40-300 μm, more preferably 40-120 μm, more preferably 40-60 μm.

In some embodiments, the fluid-impermeable member further comprises an elongate support portion attachable to a fluid loading port. In some embodiments, the cross sectional area of the fluid-impermeable member advantageously increases generally linearly relative to loading volume of solutions between a range of 300 to 600 μL into the enclosed volume.

In some embodiments, the fluid-impermeable member is formed by a polymeric material with elastic modulus of 1 kPa-10 MPa, 20 kPa-200 kPa, or 60 kPa; preferably, the polymeric material is selected from polydimethylsiloxane, EcoFlex, and NuSil polymers.

In some embodiments, the relative stiffness of the fluid resilient member is advantageously at least one order of magnitude less than the relative stiffness of the tissue supported thereon.

Optionally, the external surface of the fluid resilient member is provided with one or more topological features to guide biophysical interaction between the tissue and the tissue support. In some embodiments, the topological features are advantageously one or more of the group of topological features comprising grooves, ridges, channels, bumps, knobs, dimples, holes, pillars, and other protrusions with both rough and smooth finishes.

Optionally, the external surface is provided with patterned electrodes, or a stretch sensor.

In some embodiments, the fluid-impermeable member is formed by drop casting of a polymeric material on a 3D printed mold.

In accordance with a third aspect of the present disclosure, there is provided a method of culturing tissues, comprising the step of:

a) providing a tissue support comprising a fluid-impermeable resilient member having an external surface and defining an enclosed volume; wherein said external surface of the member is resiliently deformable by cultured tissues formed on the external surface of the member during testing thereof;

b) inflating the fluid-impermeable resilient member;

c) depositing cells onto the fluid-impermeable resilient member; and d) culturing the cells in a medium.

In some embodiments, the method comprises attaching the tissue support on to a fluid loading port via an elongate support portion of the tissue support; adding fluid to the fluid-impermeable resilient member via the fluid loading port; and/or placing the tissue support in a chamber formed in a hydrogel mold in a bioreactor.

In some embodiments, the cells are human ventricular-like cardiomyocytes derived from human pluripotent stem cells. In some embodiments, the cultured tissues are advantageously human cardiac ventricular-like organoid chambers.

In some embodiments, the testing is selected from the group consisting of a pressure-volume loop analysis, mechanical stretch measurement, electrophysiological measurement, gene expression analysis at a transcript level, gene expression analysis at a protein level, microstructural analysis using optical microscopy, and microstructural analysis using electron microscopy. In some embodiments, the electrophysiological measurements including conduction velocity, action potential duration, or conduction pattern.

In some embodiments, the testing is a pressure-volume loop analysis, a testing for studying the Frank-Starling mechanism of the cultured tissues, or a testing performed in the presence of an electric field.

In some embodiments, wherein the resilient deformation of the external surface of the member into the enclosed volume causes a measurable change in the cross sectional area and enclosed volume of the member.

In some embodiments, the fluid-impermeable member defines a substantially spherical enclosed volume in an inflated state, and/or the fluid-impermeable member is formed as a generally spherical balloon in an inflated state. In some embodiments, the inflation of the fluid-impermeable member allows the enclosed volume to assume a predetermined size and shape.

In accordance with a fourth aspect of the present disclosure, there is provided a method of fabrication of a tissue support comprising a fluid-impermeable resilient member having an external surface and defining an enclosed volume; the method comprises the steps of:

a) forming a thin film of polymer on a mold;

b) curing the polymer to form the tissue support; and c) removing the tissue support from the mold;

wherein said support comprises a resilient external surface of the member that is resiliently deformable by cultured tissues formed on the external surface of the member during testing thereof.

In some embodiments, the polymeric material has elastic modulus of 1 kPa-10 MPa, preferably 20 kPa-200 kPa, or 60 kPa; in some embodiments, the polymeric material is selected from polydimethylsiloxane, EcoFlex, and NuSil polymers.

In some embodiments, the mold comprises a generally spherical portion, and an elongate portion, attachable to the sphere shaped portion. Optionally, the mold has a shape derived from 3D medical imaging techniques.

Optionally, the external surface of the mold comprises one or more topological features to guide biophysical interaction between the tissue and the balloon. In some embodiments, the topological features are advantageously one or more of the group of topological features comprising grooves, ridges, channels, bumps, knobs, dimples, holes, pillars, and other protrusions with both rough and smooth finishes.

In some embodiments, the mold is formed by 3D printing or milling. Optionally, the mold is dissolvable.

In some embodiments, the thin film of polymer is fabricated on the mold by drop-casting, dip-coating, injection mold, lost-wax casting or soap casting.

In some embodiments, the method is advantageously provided as an automated high-throughput process.

BRIEF DESCRIPTION OF THE FIGURES

In order to describe the manner in which the above-recited and other advantages and features of the disclosure can be obtained, a more particular description of the principles briefly described above will be rendered by reference to specific embodiments thereof which are illustrated in the appended figures. Understanding that these figures depict only exemplary embodiments of the disclosure and are not therefore to be considered to be limiting of its scope, the principles herein are described and explained with additional specificity and detail through the use of the accompanying figures.

Preferred embodiments of the present disclosure will be explained in further detail below by way of examples and with reference to the accompanying figures, in which:—

FIG. 3 depicts the approximate elastic modulus of various tissues.

FIG. 4A depicts an exemplary tissue support member in a deflated state.

FIG. 4B depicts an exemplary tissue support member attached at the end of the fluid loading port in an inflated state.

FIG. 11A depicts steps in an exemplary drop-casting process for making an embodiment of the liquid impermeable tissue support member.

FIG. 11B depicts an exemplary drop-casting method for depositing the selected polymer on the master mold in preparation of the EcoFlex polymer onto a stereolithography (SLA) 3D printed master mold.

FIG. 12A depicts an exemplary method for taking thickness measurements of exemplary drop cast tissue support members (in the embodiment depicted balloons) and cross-sectional profiles.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

In a broad aspect of the present disclosure there is provided a tissue support, which may be known as a "tissue scaffold", "substrate", or "tissue engineering platform", for culturing tissues that can be retained inside the cultured tissues during testing, enabling the production of impermeable and uniform tissues and organoids formed thereon.

Testing may be performed on balloon-supported tissues that are (1) either unloaded, loaded acutely, or have been loaded chronically, (2) either spontaneously beating or being stimulated via an electric field or point stimulus, (3) either in control conditions or have been exposed to different concentrations of drugs or other soluble compounds, and (4) cultured on balloons that have a uniform composition and topology over its surface, or with localized regions of different composition or topology to induce localized responses. Exemplary types of testing that may be performed include: pressure-volume loop analysis; mechanical stretch measurements; electrophysiological measurements including conduction velocity, action potential duration, conduction pattern; gene expression analysis at transcript and protein levels; and microstructural analysis via optical or electron microscopy.

Optical conduction mapping can also be performed on the live chamber if a voltage sensitive dye or other voltage reporter molecule is added which allows one to visualize changes in membrane potential and therefore, calculate conduction velocity across the tissue. Similarly, optical contractility mapping can be performed using calcium-sensitive dyes or reporter molecules to visualize patterns of contractile activity. After functional chamber studies are complete, tissues can be removed and imaged for cellular alignment and orientation, measured for thickness and tissue modulus, digested and used to study cellular and protein composition and or for PCR/Western Blot measurements.

Figure 1:
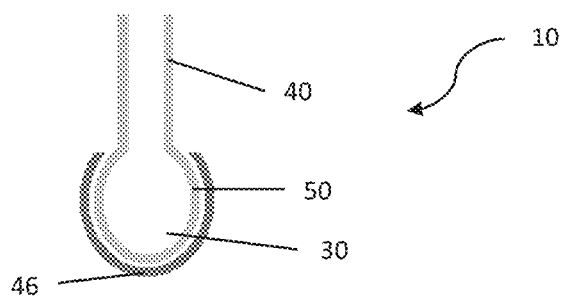
FIG. 1 depicts a schematic representation of an exemplary tissue support with cultured tissue according to an embodiment of the present disclosure.

Referring to FIG. 1, there is depicted an exemplary tissue support according to an embodiment of the present disclosure. The tissue support 10 comprises a fluid-impermeable resilient member 50 which defines an enclosed volume 30. In this figure, the tissue support is in an inflated state and fluid-impermeable resilient member is provided as a spherical-shaped balloon with an elongate neck portion 40. The tissue support may be inflated by the addition of fluid (e.g. water) into the enclosed volume via the elongate neck portion, which is configured to be attachable at one end to a fluid loading port.

The spherical-shaped balloon 20 depicted in FIG. 1 can be used as a mold for the fabrication of cardiac organoid chambers, also known as a "3D heart". However, it can be understood that the tissue support of the present disclosure can be provided in different sizes and shapes suitable for the fabrication of organoid constructs adapted to the properties of a number of human tissues or organs, including blood vessels, lung, bladder, intestine, trachea, uterus, and numerous other hollow organs.

The term "balloon" is used interchangeably with the term "fluid-impermeable resilient member" herein, nonetheless, it would be appreciated by persons skilled in the art that the fluid-impermeable resilient member is not limited to a balloon. Advantageously, the shape of the fluid-impermeable resilient member can be created based upon the required organoid constructs in accordance with known tissue engineering techniques.

In an embodiment, the fluid-impermeable member is formed by drop casting of a polymeric material on a 3D printed mold, which may resemble the shape of a miniature version of anatomical heart shape, which may be derived from 3D medical imaging techniques, such as MRI.

As shown, the fluid-impermeable resilient member has an external surface for supporting the growth of cells deposited thereon, allowing the formation of tissues 46 compacting around the external surface of the resilient member 10. The external surface of the member is resiliently deformable by the cultured tissues formed on the external surface of the member during testing of the tissue. Such tests include any typical tests that are used to examine the mechanical properties of tissues of the particular organ of interest; and in the case of cardiac tissues, including PV loop analysis, test for investigating the Frank-Starling mechanism, as well as tests involving an electric field for stimulation of the tissue construct.

During testing of the cultured tissues, an increased hydrostatic loading in the enclosed volume stretches the cardiac tissue. The resilient deformation of the external surface of the member into the enclosed volume causes a measurable change in the cross sectional area and enclosed volume of the member. Since the fluid-impermeable member is able to prevent leakage during loading, it is possible to apply a direct loading, and allows for consistent physiologically-related measurements like pressure-volume relationship.

Compared to the use of commercial balloon catheter in the preparation of tissue constructs, the resilient member of the present disclosure acts like a "thin permanent lining" for the tissue construct—due to its softness, the member can be retained inside the tissue throughout culture and testing without requiring inflation pressure to maintain its intended shape (e.g. spherical shape), and without interfering with tissue contraction and affecting the measurements. This in turn eliminates the leakage problem often seen in tissue constructs formed using balloon catheters, especially as the balloon catheter is removed for conducting the test to allow the tissue to contract during beating. Preventing leakage allows precise control and maintenance of loading pressures on organoid chambers during testing. Additionally, since the resilient member is provided in a customizable shape with a general consistent wall thickness, it allows the formation of organoids of increased uniformity as compared to organoids formed on a removable balloon catheter.

Figure 2A:
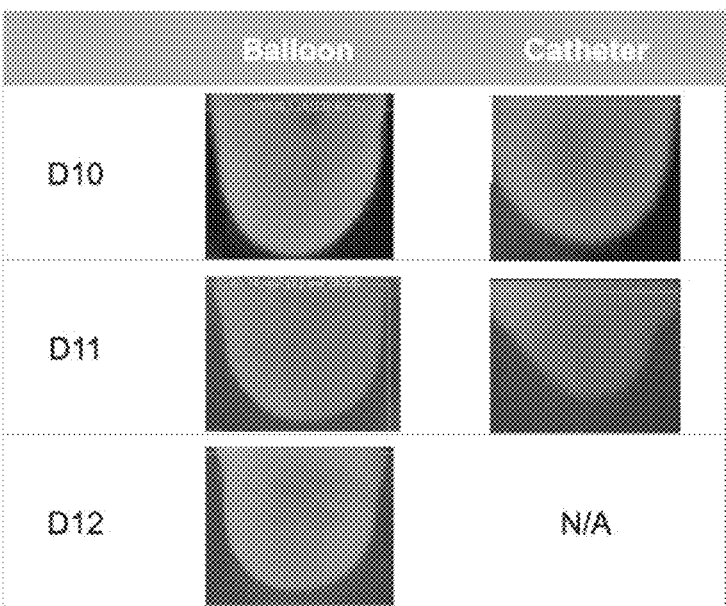
FIG. 2A illustrates the difference in shape of tissue chamber formed with an exemplary tissue support of FIG. 1 (which remains within the chamber), compared with a tissue chamber formed over a balloon catheter over time (after the balloon catheter has been removed). N/A indicates not applicable as the tissue was unable to be measured on this day due to collapse.
Figure 2B:
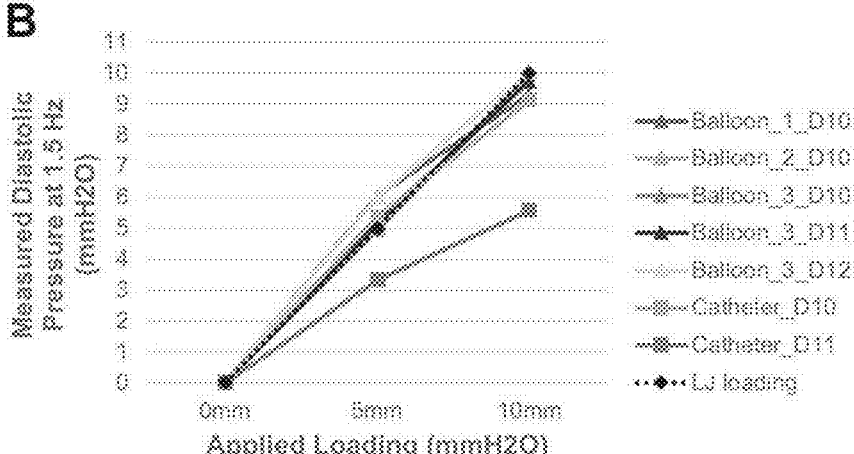
FIG. 2B depicts the relationship between diastolic pressure and applied loading in tissue chambers under different conditions and configurations. LJ loading indicates the system used to apply hydrostatic loads to both the balloon and the catheter tissues.
Figure 2C:
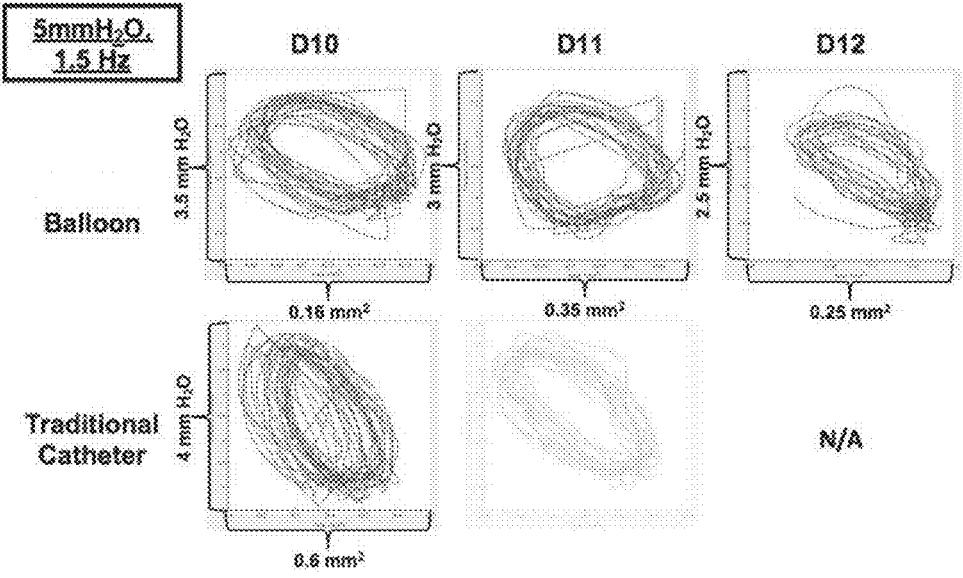
FIG. 2C depicts the pressure-volume loops (PV loops) for an embodiment of the tissue support formed from the balloon (Eco and silicone filler) of the present disclosure as compared to prior art (withdrawn) tissue support member (traditional catheter) during repeated testing on days 10, 11, and 12.

FIG. 2A-2C provides a direct comparison of tissues fabricated on the retained resilient member of the present disclosure compared with tissues fabricated using a balloon catheter (which is subsequently withdrawn). As shown in FIG. 2A, the catheter based tissue preparation began to compact on itself over time after the catheter was removed (see photographic representations of the tissue constructs on days 10, 11, 12). At Day 12, the tissue made without the internal resilient tissue support of the present disclosure in place throughout testing compacts to the point where it cannot be measured. As such, due to over-compaction of tissue, no result is provided for the tissue made with balloon catheter in the prior art (which is removed before testing).

Furthermore, as depicted in FIG. 2B, the tissue construct prepared with a resilient member retained inside the tissue construct demonstrates an almost linear relationship between the applied loading and the observed diastolic pressure, as compared to tissue construct prepared with the traditional method which is unable to be loaded over time. In particular, the prior art tissue chamber formed over a (withdrawn) catheter was unable to be properly loaded for the prior art on Day 11, as indicated by substantial deviation from the expected 1:1 relationship between measured and applied pressure, indicated by the heavy dashed line. In FIG.

2C, the D11 measurement for this chamber is faded as due to tissue failure over time, it could not be loaded with 5 mmH$_2$O when measured like the other data presented in the figure. The N/A for D12 for this same chamber indicates it could not be measured on this day as tissue continued to compact and deteriorate over time. For this loaded testing, both balloon and catheter preparation were loaded with the LJ system originally designed to load leaking tissues prepared via the catheter method. The LJ system connects a liquid line from the chamber through the fluid port to a liquid reservoir on a jack system. By adjusting the liquid reservoir height relative to the position of the chamber, the hydrostatic load can be adjusted to increase pressure in the chamber.

As further discussed in the example section below, PV loop analysis was conducted comparing the tissues fabricated with the tissue support of the present disclosure with those fabricated using a balloon catheter with the catheter withdrawn. The benefit of the present disclosure becomes apparent when testing the tissue chambers over time as the tissues prepared in accordance with the present disclosure are more stable and consistent with repeated measurements as shown by the consistently overlapping loops in FIG. 2C. The results demonstrate that the tissue support of the present disclosures enables the production of tissues that can provide accurate measurement over time (providing clean signals) over an extended period of time, making it well-suited as a drug testing platform.

Properties of Resilient Member

In order to fabricate a fluid-impermeable resilient member that is compressible by tissues and can be left in place during measurement, the resilient member needs to be formed using a thin layer of soft material with a specific stiffness. FIG. 3 illustrates the relative stiffnesses of various tissues; modulus values given in Pa (adapted from Cox, et al. [13]).

In order to approximate the needed thickness of the balloon given a material modulus initially, it was first assumed that the thickness of balloon needed to be such that it stretched at least as much as the tissue chamber alone did when loaded internally. Therefore, given an internal pressure during loading, the change in radius of balloon must be equal to the change in radius of the tissue chamber. Hoop stress formula for a thin walled hollow sphere relates the tangential stress in the balloon shell ($\sigma_t$) to the balloon thickness ($h_o$), initial radius ($r_o$), final inflated radius ($r_f$) and difference in pressure between inside and outside of the balloon (p):

$$\sigma_t = \left(\frac{r_f}{r_o}\right)^3 \left(\frac{r_o p}{2h_o}\right) \qquad \text{Eq. 1}$$

Hoop stress can also be written as a function of the material modulus, E, and Poisson's ratio, $\nu$ (assuming linear elastic behaviour) and the circumferential strain, $\epsilon$ (set equal to strain in the tissue):

$$\sigma_t = \frac{\epsilon E}{1 - \nu} \qquad \text{Eq. 2}$$

$$\epsilon = \frac{\Delta Circ}{Circ_o} = \frac{r_f - r_o}{r_o} \qquad \text{Eq. 3}$$

Using chamber data from other studies conducted in the lab, a value for change in diastolic radius ($\Delta r$) with change in diastolic pressure ($\Delta p$) provides an approximate value of:

$$\frac{\Delta r}{\Delta p} \sim 0.05 \frac{\text{mm}}{\text{mm} \ \text{H}_2\text{O}} \qquad \text{Eq. 4}$$

Based on these assumptions, the balloon thickness ($h_o$) as a function of material modulus (E) is derived to be the following:

$$h_o = \frac{r_f^3 p(1 - \nu)}{2r_o E(r_f - r_o)} \qquad \text{Eq. 5}$$

In this equation, the initial radius ($r_o$) is assumed to be the starting radius of the balloon and the final radius ($r_f$) is calculated using the $$\frac{\Delta r}{\Delta p}$$

value stated in Eq. 4. The loading pressure (p) is 5 mmH$_2$O.

Using this equation, it is possible to approximate the necessary balloon thickness ($h_o$) to allow the balloon to expand under load, assuming a given material and modulus. Initial approximations for the two exemplary materials used as examples are shown in Table 1 alongside the achievable thicknesses.

TABLE 1

|  | Ecoflex 00-30 | Ecoflex 00-30 + 20% Silicone Filler |
|---|---|---|
| Modulus | 60 kPa | 25 kPa |
| Target thickness | 14.3 µm | 34.3 µm |
| Achieved thickness | 60 µm | 80 µm |

These approximated values ended up being smaller thicknesses than were needed for the dynamic movement seen during contraction, as demonstrated by the PV data generated for both materials at the achieved thicknesses. This indicates that PV data generated with the balloon present may not be representative of the maximum stroke areas achievable. To calculate a range of tissue to balloon stiffnesses, a stiffness value of a give material is assumed to be a product of its modulus and thickness.

TABLE 2

|  | Tissue Thickness (µm) | Tissue Modulus (kPa) | Stiffness Value (Thickness*Modulus, µm*kPa) |
|---|---|---|---|
| Current | 100 | 20 | 2000 |
| Maximum | 400 | 20 | 8000 |

|  | Balloon Thickness (µm) | Balloon Modulus (kPa) | Stiffness Value (Thickness*Modulus, µm*kPa) |
|---|---|---|---|
| Current | 60 | 60 | 3600 |
| Maximum | 20 | 20 | 400 |

| Case | Ratio |
|---|---|
| Current Tissue to Balloon Stiffness Ratio | 0.6 |
| Improved Balloon to Current Tissue Stiffness Ratio | 5.0 |
| Max Fold - Improved Tissue and Balloon Ratio | 20.0 |

The top section of Table 2 shows the tissue and balloon thicknesses and moduli used to calculate the respective stiffness values as products of these two numbers. The bottom of the table shows the current, improved, and best case stiffness ratios (calculated from the stiffness values of the current and best case tissues and balloons). Ideally, the balloon stiffness should be an order of magnitude less than the tissue as to not interfere at all in the motion or behaviour of the organoid supported thereon.

Depending on the tissue construct required, the tissue support can be provided with a generally consistent wall having a thickness of approximately 40-300 µm, preferably 40-120 or 40-90 µm, more preferably 40-70 µm. Preferred thickness of members made from EcoFlex 00-30 for cardiac organoids is 40-60 µm. As would be appreciated by those skilled in the art, tissue support with thicker walls can be provided by multiple rounds of material deposition and curing, and tissue support with thinner walls can be created by a single layer deposition. To decrease the thickness of single layer deposition, mold geometry and or surface finish could be tailored to enhance the rate of flow down the mold. A decrease in material viscosity should also decrease this wall thickness.

Suitable materials for use in the fabrication of the tissue support include polymeric materials (e.g. silicone) having an elastic modulus of 1 kPa-10 MPa, preferably 20 kPa-200 kPa, and more preferably 60 kPa. However, as stated previously, member interference with the tissue's contraction would only be further reduced and measurement capabilities enhanced with the introduction of even softer, impermeable, biocompatible materials.

Examples of suitable soft polymers include soft hydrogels, PDMS (Sylgard 184 and 527, Dow), EcoFlex 00-10 and 00-30 (SmoothOn), NuSil polymers (MED10-6600, MED10-6605), and mixtures thereof. Optionally, additives such as Xiameter (a silicone filler material), MicroLubrol 200 Fluid Pure Silicone Oil Polydimethylsiloxane (PDMS) 100 centistokes (cst) viscosity can be added.

Advantageously, the fluid-impermeable resilient member of the present disclosure provides an "interface with the supported tissue", giving the option for the user to interact with the tissue at the balloon cell interface via physical cues, such as a textured surface or electrical cues such as patterned electrodes. In an embodiment, external surface of the member may be provided with one or more topological features to guide biophysical interaction between the tissue and the balloon. Such topological features can be in the form of grooves and ridges to enhance cellular alignment and general patterning of the cells. Protruding features from the balloon surface or changes in surface texture could be used to introduce imperfections in the attached tissue surface, mimicking different diseased or injured tissue states or introducing arrhythmic behavior when the tissue is stimulated.

Similarly, regions or protrusions from the balloon surface could be modified (e.g. coating or embedding) with conductive material to provide localized, conforming electrodes that allow for electrical interactions with or readouts from the tissue. Indentations or protrusions with divots could be used to enhance the attachment of tissue to the surface of the balloon by allowing for ingrowth or better encapsulation by the tissue. Exemplary topological features include grooves, ridges, channels, bumps, knobs, dimples, holes, pillars, other protrusions with both rough and smooth finishes.

In another embodiment, the external surface of the member is provided with (e.g. by printing or masked sputter coating) electrodes (similar to microelectrode array) that conform to the shape of the organoid chamber and are able to stimulate and measure electrophysiological parameters (such as conduction velocity) or arrhythmic events of the tissue thereon. This allows the measurement of electrophysiological signals and functional readouts simultaneously without the necessity of biochemical electromechanical decoupling (e.g., treating with blebbistatin or BDM), and stimulation of the tissue in specific locations and monitoring of signal propagation to examine conduction velocity and arrhythmogenic conduction patterns (e.g., spiral waves).

In another embodiment, the external surface is provided with a stretch sensor for stretch measurement.

For example, a metal trace of two or more metals can be deposited onto prestressed thermoplastic materials. When heat is applied and the plastic begins to subsequently shrink, the stiffness mismatch between the plastic and metal film causes the metal to buckle into multiscale wrinkled structures. The overall dimension of the metallic trace shrinks in proportion with that of the plastic. The multiscale wrinkled features allow the metal thin film to behave more similar to its bulk material counterpart. This increases the sensitivity in detecting electrical changes when the sensor is physically strained or similarly its gauge-factor [15]. In applying this to the tissue support, a similar strain gauge could be fabricated by overinflating the resilient member prior to metal deposition and then allowing it to deflate, thereby buckling the metal. To create flexible electrodes to pick up electrophysiological signals on the external surface of the resilient member, this mechanism could also be leveraged. Different methods for detecting tissue stretch during contraction could leverage other sensing technologies that might be embedded on the surface or inside the member. These could include magnetic particles that during movement affect the electrical readouts from a Hall effect, GMR, or other magnetic sensor where resistance to current flow changes in the presence of a magnetic field. A capacitance sensor could also be built into the system where metal sensing plates are positioned around the outside of the balloon and targets to be sensed are embedded into the balloon surface. If these are electrically connected, the electrostatic field between them, which changes during contraction and movement of the balloon surface, would be affected by the distance between the two sensing elements.

In another embodiment where the tissue to be prepared is intended for disease modeling applications, the resilient member of the tissue support can be provided with an area of different stiffness at a localized region to mimic damaged or dead myocardium. This means that the resilient member has a localized region that deforms either more or less to a force applied thereon as compared to the areas immediately surrounding the localized region. The resilient member may include small holes at specific region on its surface that only leak during expansion, providing a selective dosing mechanism that allows the delivery of internal solution to desired locations on the tissue.

In a yet further embodiment, the external surface of the resilient member may be chemically modified with proteins (by either covalent or non-covalent bonding) for increasing cell binding/maturation.

Preparation of Tissues

Referring to FIG. 4A, there is provided a tissue support 60 of the present disclosure, where the fluid-impermeable resilient member 50 depicted is in its deflated state. The support 60 can be attached to a fluid loading port by attaching an elongate support portion 52 onto the end of a hollow attachment tubing 54 as depicted in FIG. 4B, which shows the resilient member 50 at its inflated state.

Figures 4C, 4D, 4E:
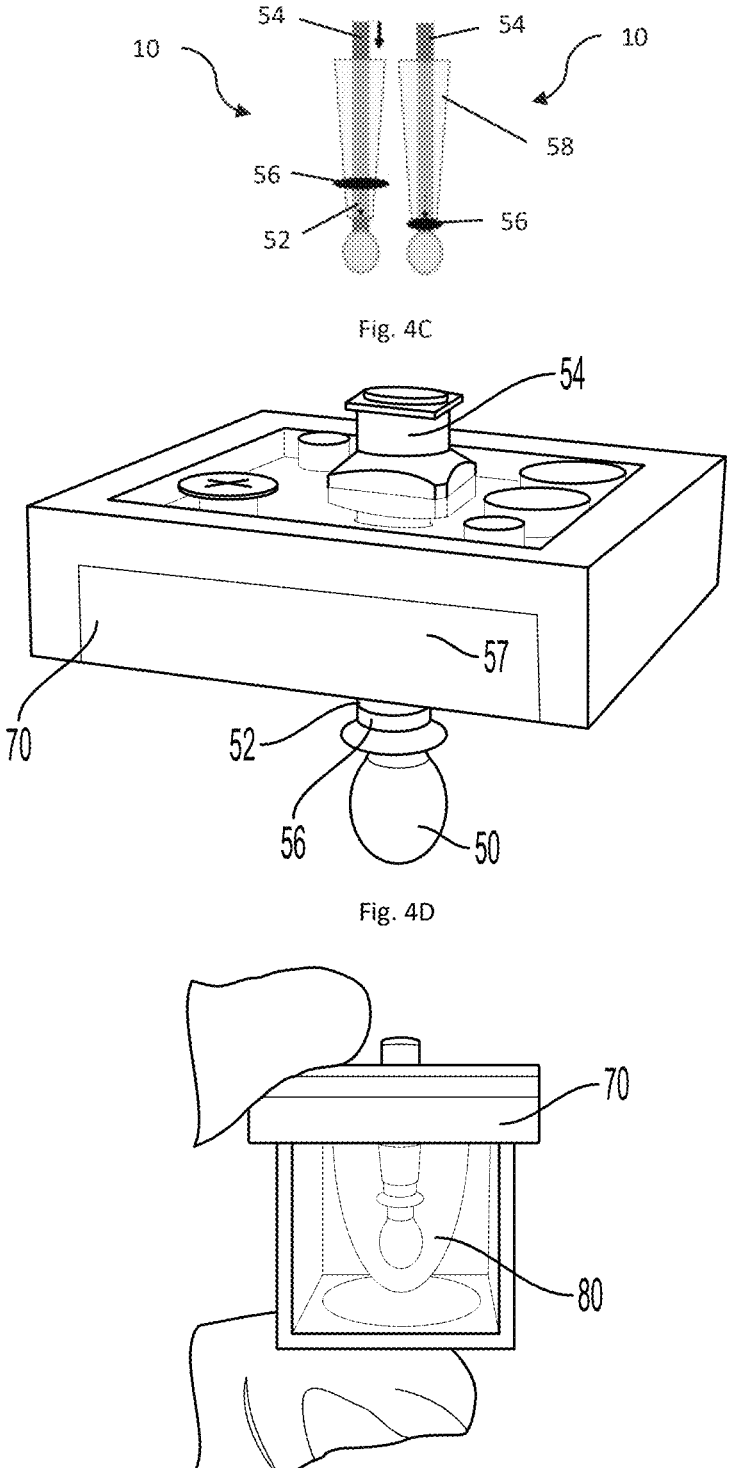
FIG. 4C depicts an exemplary method for attaching the O-ring onto the tissue support member.
FIG. 4D depicts an exemplary bioreactor setup including various components for securing an exemplary tissue support member (balloon) to the attachment/loading hardware and facilitating tissue attachment to the neck.
FIG. 4E depicts a hydrogel outer mold with an exemplary balloon placed inside.
Figure 4F:
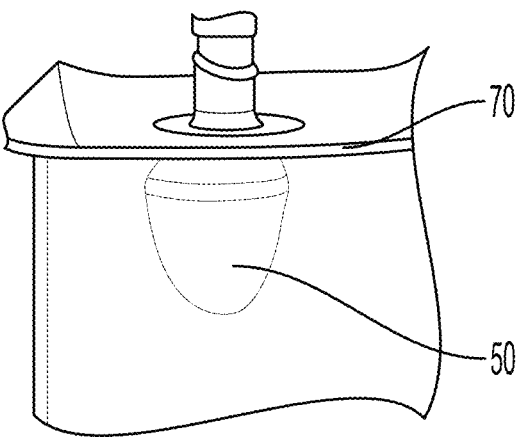
FIG. 4F depicts compacted tissue around the exemplary balloon.

Advantageously, as depicted in FIG. 4C, a resilient O-ring 56 is stretched and slid onto the elongate neck portion 52 of the resilient member 50, e.g. by the use of a 1 mL pipette 58, such that it is placed on the attachment tube 60 (also described herein as the loading hardware) above the base to hold and seal the resilient member 50 in place.

As shown in FIG. 4C, a porous polymeric ring 57 is also slid over the resilient member 20 and placed just below the O-ring for tissue attachment. Upon filling the resilient member 50 with the appropriate volume of fluid to form its intended shape, the resilient member (balloon) 50 and attachment tubing 54 are fit into the lid of a bioreactor vial. Optionally, a parafilm 59 can be placed on top of the opening of the attachment tubing to reduce water vaporization from the balloon cavity.

Figure 8A:
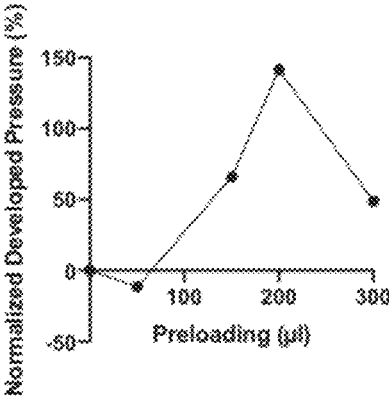
FIGS. 8A, B and C illustrate the normalized developed pressure, stroke area, and stroke work for the different loading conditions shown in FIG. 7.

A bioreactor box 70 with a hydrogel having an air pocket 80 configured for receiving the tissue support is used for tissue culture as depicted in FIG. 4D. Upon placing the tissue support in the bioreactor box 70, a cell mixture solution comprising the required cells is deposited on the external surface of the fluid-impermeable resilient member, allowing the growth of cells in a suitable medium to form the required tissues and organoids. As depicted in FIG. 8F, tissues form on the balloon as depicted in FIG. 4E, which shows human ventricular Cardiac Organoid Chamber (hvCOC) chambers compacting around the balloon.

In a preferred embodiment, human ventricular-like cardiomyocytes (hvCMs) are derived from human pluripotent stem cells (hPSC) to obtain spontaneously contracting cardiomyocytes. Dissociated and reaggregated cardiospheres of spontaneously beating human ventricular-like cardiomyocytes (hvCMs) are mixed with Human foreskin fibroblasts (HFF) to form the cellular mixture. The cellular mixture may comprise of one or more of the following to support the growth of cells: collagen, NaOH, 10× Minimum Essential Medium (MEM), HEPES, Newborn Calf Serum (NCS, 10%) and Matrigel, and NCS growth medium.

In a further embodiment, the balloon from beneath can be inflated during cell sheet growth. In particular, it has been known that rolled sheets of aligned cells can be used to form a chamber, so as to improve the strength and physiological relevance of the tissue [12]. In using the balloon of the present disclosure to achieve a similar end result, a sheet of cells would be grown onto the top of a deflated balloon. As the sheet of cells forms, it is expected that the balloon would slowly be inflated from below to encourage the sheet to fall down the sides of the balloon and adopt the shape.

In a further embodiment, the balloon can be loaded over an extended period of time (as to mimic a stressed or diseased state) after tissue formation around the balloon by adding additional fluid into the defined volume via the fluid loading port. Traditionally, these hvCOC preparations without an indwelling balloon are not stable enough to hold hydrostatic loading without leakage, therefore, an additional liquid reservoir is required to maintain pressure and expansion. This condition is cumbersome to achieve in an incubator for extended culture under controlled environmental conditions.

However, in the tissue support of the present disclosure, the ability to load the attachment tubing without leakage, afforded by the indwelling balloon, allows loading of the hvCOC to be applied over long periods of time without additional complicated components.

In yet a further embodiment, oscillations in loading could be provided during culture to modulate maturation, resembling a system with a cyclically inflated and deflated balloon for enhancing the maturation of the engineered tissue. A similar idea has been applied to sheets of cells in products from FlexCell [15].

Properties of Fabricated Tissues

The fabricated tissue formed by the use of the tissue support of the present disclosure is healthy and stable-remaining viable for up to 30 days supported on the resilient member/balloon member. Tissue contraction is strong enough to visibly compact the underlying balloon during beating, causing a measurable change in cross-sectional area and internal pressure.

Figure 5A:
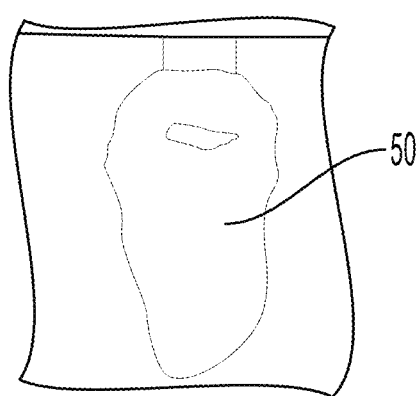
FIG. 5A depicts the compaction of tissue with an exemplary tissue support member as the member is being deflated.
Figure 5B:
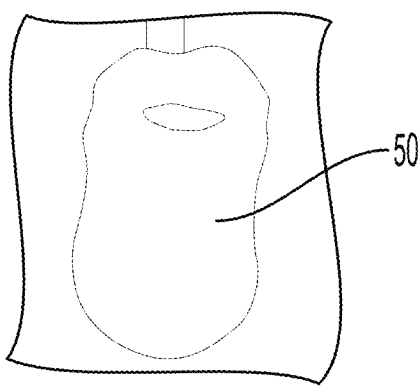
FIG. 5B depicts an exemplary view of the tissue as the exemplary support member is inflated, being supported by and tracking with the support member during inflation.

FIGS. 5A and 5B are photographs of exemplary fabricated tissue when the underlying balloon 50 is at a deflated and an inflated state respectively. FIG. 5A shows the compaction of tissue as liquid is drawn out of the balloon, indicating the tissue is attached to the member and follows that member even for small changes in volume. As depicted in FIG. 5B, tissue maintains tracking with the balloon during/after inflation.

Figures 1, 6A:
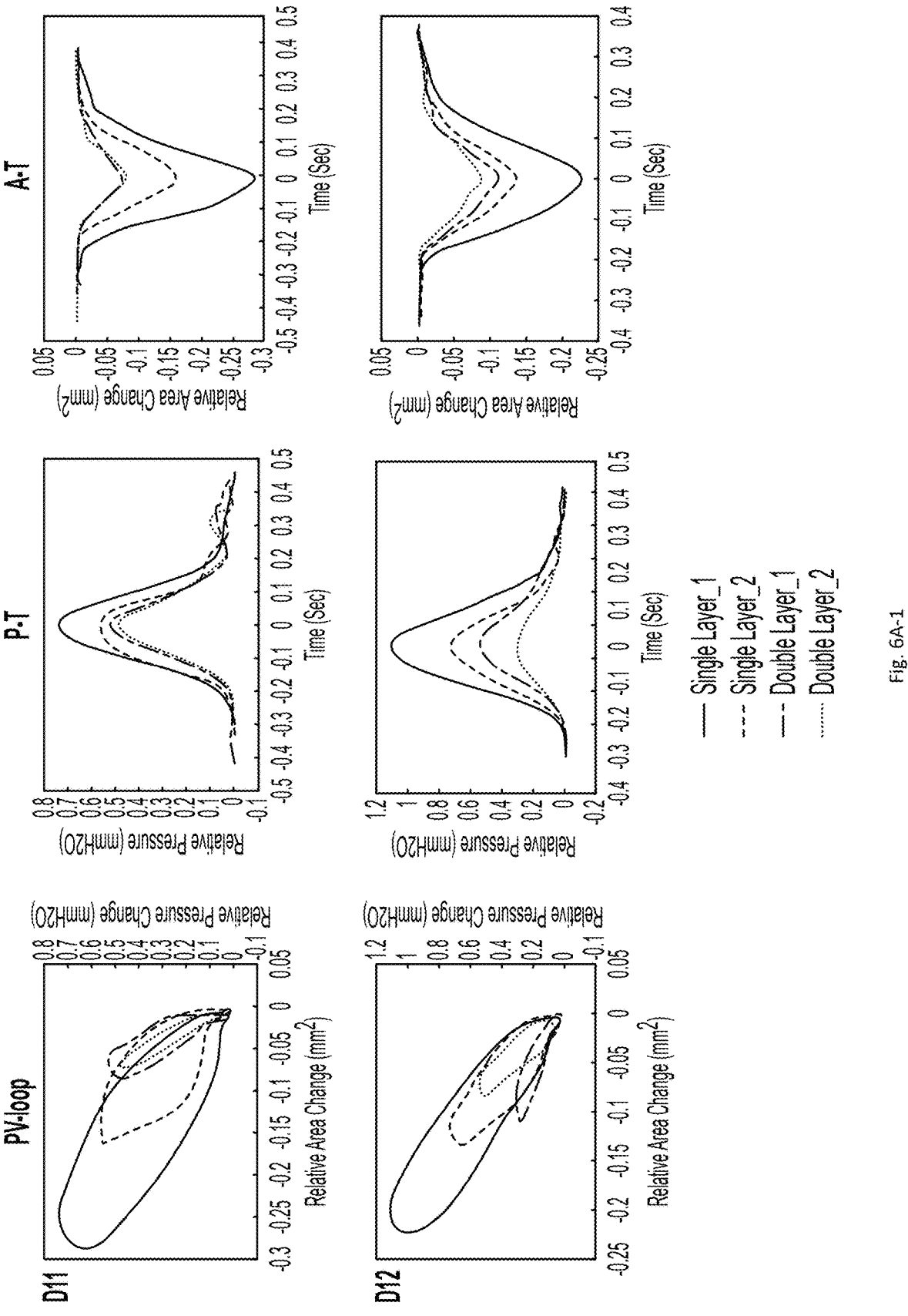
FIG. 6A depicts various PV loop results of a single layer and a double layer tissue support member on successive days.
Figures 2, 6A:
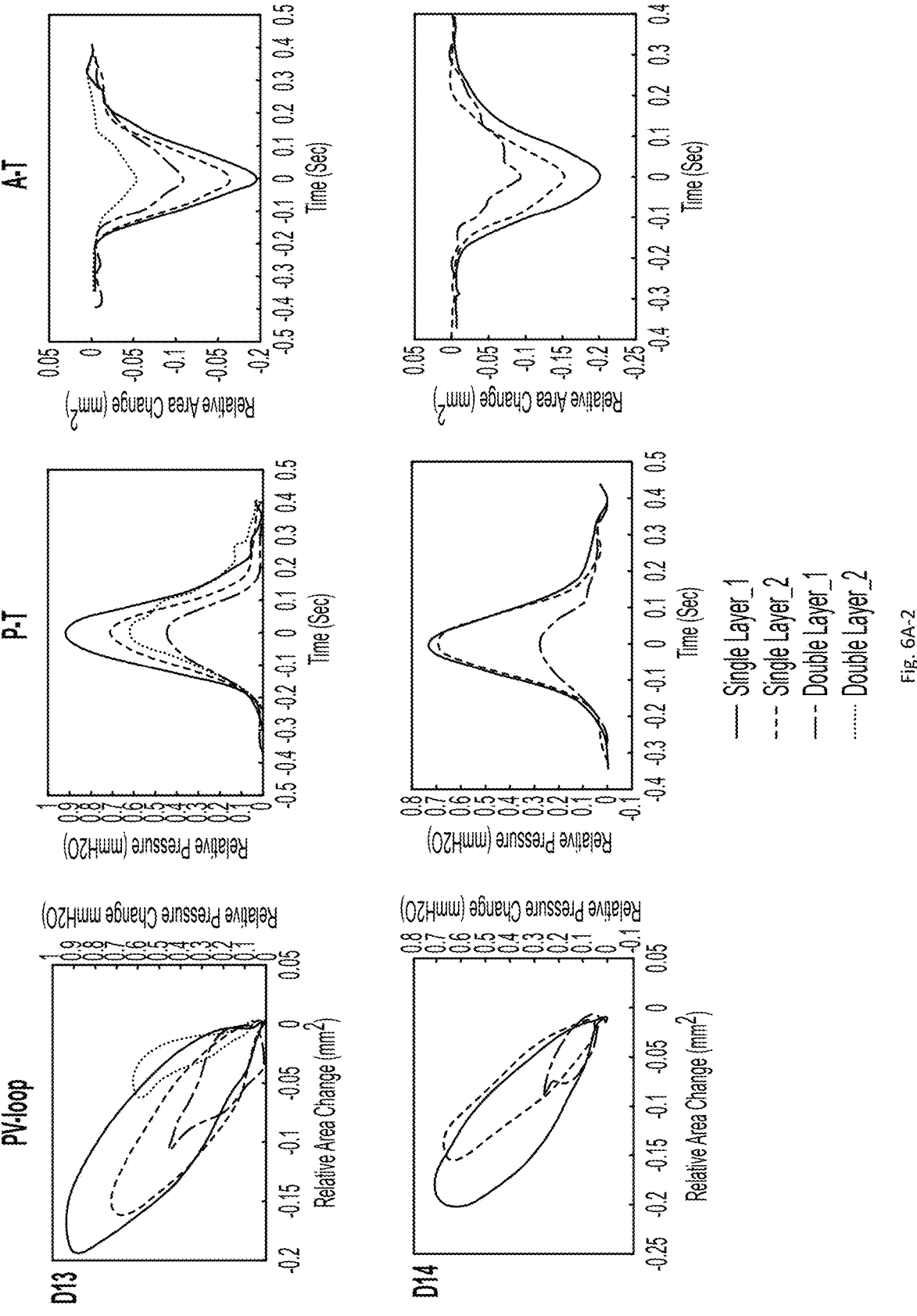
Figure 6B:
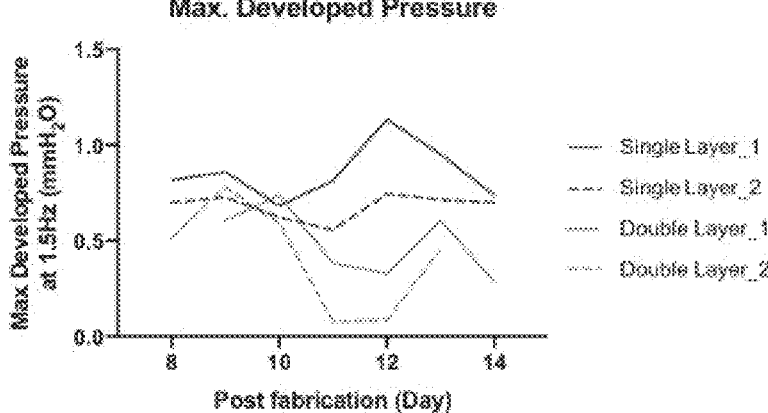
FIG. 6B illustrates the maximum developed pressure and area of single layer and double layer tissue support members. The top plot is the developed pressure, which is measured via a pressure probe placed inside the balloon. The bottom plot is the change in the size of the cross-sectional area as imaged from the side of the chamber and is related to change in chamber volume. The relative stability of both signals over time indicates that the chambers' beating forces and profiles are fairly consistent over multiple days of testing as compared to chambers fabricated with the previous catheter technology.
Figure 6B:
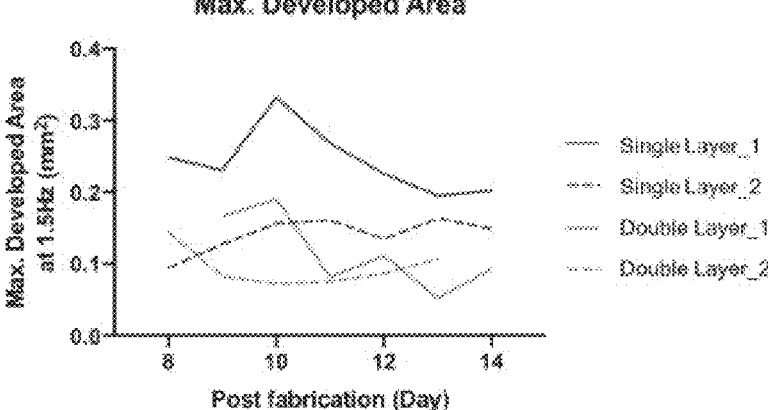

Tissues fabricated using a single layer balloon (Ecoflex) was compared to tissues fabricated using a double layer balloon (Ecoflex+silicone filler). As depicted in FIGS. 6A and 6B, both tissues show sustained contractile performance over time, based on representative PV loops as well as pressure-time (P-T) and area-time (A-T) tracings, but the developed pressure and stroke area of the single layer balloon tended to be larger, suggesting that the single layer EcoFlex balloon ultimately allows for better tissue response when compared to those made from the double layer balloon of composite material.

Figure 7A:
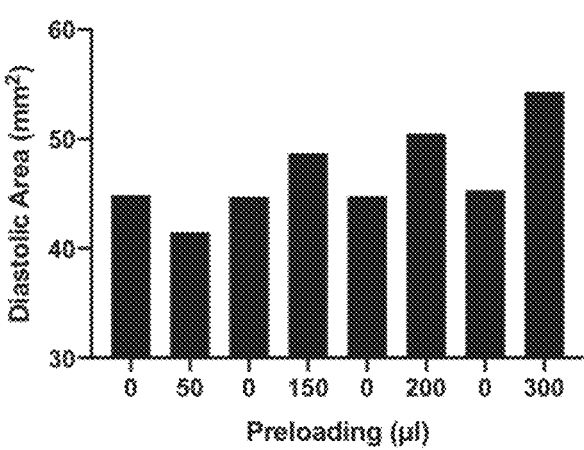
FIGS. 7A and 7B depict the changes of diastolic area and pressure with increased loading of the enclosed volume through the attachment tubing.
Figure 7B:
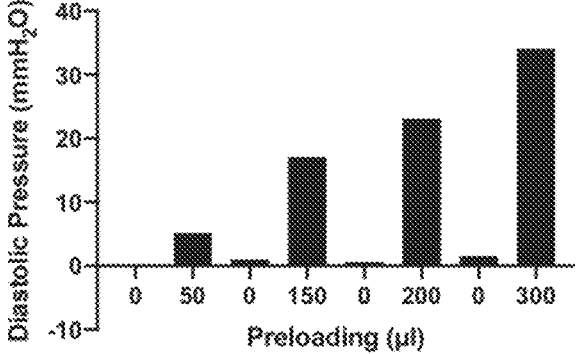
Figure 8B:
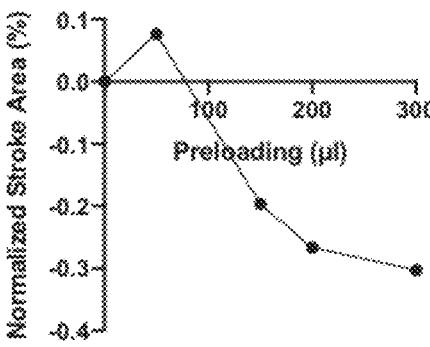
Figure 8C:
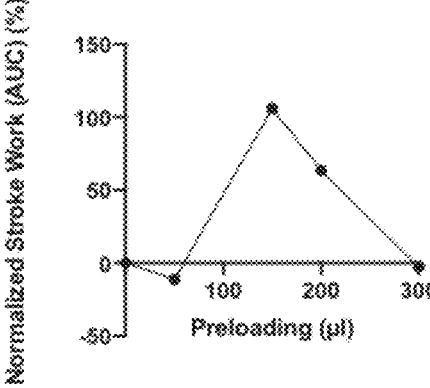

Further tests were conducted to examine Frank-Starling mechanism of the cardiac organoid chambers formed according to the present disclosure. FIG. 7 depicts that the changes in diastolic area and pressure with increased loading of the chamber through the attachment tubing. Normalized developed pressure, stroke area, and stroke work for the different loading conditions shown in FIGS. 7A and 7B are provided in FIG. 8A-C. These results indicate that the tissues demonstrate some response to loading as shown by the increase in developed pressure with increased loading.

Figure 9A:
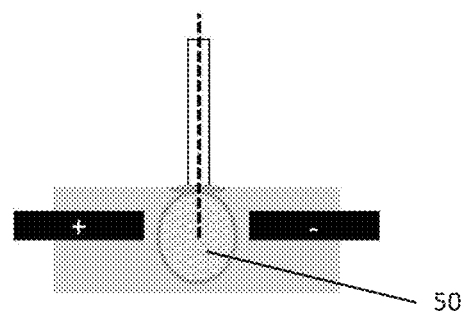
FIG. 9A depicts an experimental setup for measuring electric signals inside the tissue support member during electrical field stimulation in the external bath to control human ventricular Cardiac Organoid Chamber (hvCOC) beat rate.
Figure 9B:
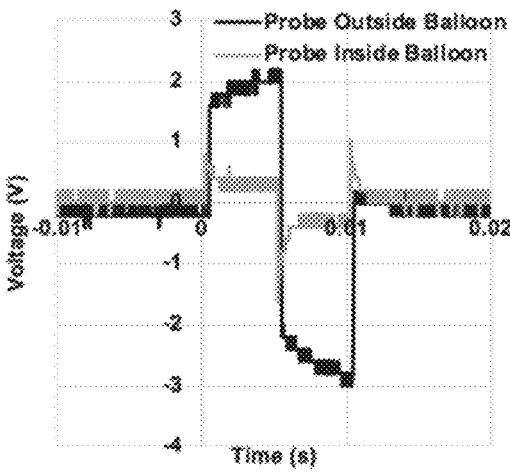
FIG. 9B depicts the voltage profiles measured inside and outside of the tissue support member.

A further experiment was performed to investigate the electric signals inside the balloon during electrical field stimulation in the external bath to control hvCOC beat rate, as depicted in FIG. 9A. Voltage profiles measured inside and outside of the balloon as depicted in FIG. 9B suggest that the balloon may provide an insulating layer that can shield the inside environment from the surroundings, making the balloon particularly useful for tests that require pacing tissues at different frequencies with electric field where the user would like to use probes or instruments sensitive to or damaged by this electric field. These could still be used for measurement inside the member.

Fabrication of Tissue Support

Further described herein is a method for creating a tissue support comprising the fluid-impermeable resilient member. The method involves the step of forming a thin film of polymer on a mold; curing the polymer to form the tissue support; and removing the tissue support from the mold. The thin film of polymer may be formed on the mold by drop-casting, dip-coating, injection mold, lost-wax casting, or soap casting. Suitable materials for use in the fabrication of the tissue support include polymeric materials (e.g. silicone) having an elastic modulus of 1 kPa-10 MPa, preferably 20 kPa-200 kPa, and more preferably 60 kPa. Examples of suitable soft polymers include soft hydrogels, PDMS (Sylgard 184 and 527, Dow), EcoFlex 00-10 and 00-30

(SmoothOn), NuSil polymers (MED10-6600, MED10-6605), and mixtures thereof as described above.

Advantageously, the polymer is cured at a temperature of 70-140° C., preferably 80-120° C., more preferably 90-110° C., and most preferably 95-105° C., for 5-60 minutes, preferably 10-50 minutes, more preferably 20-50 minutes, and most preferably 30-35 minutes.

In an embodiment of the present disclosure, the polymer is formed around a melt-able or dissolvable mold that can be removed via temperature, water, or solvent. The mold may be made with 3D printers (such as Stereolithography 3D printing) or with milling or other machining techniques.

Figure 10A:
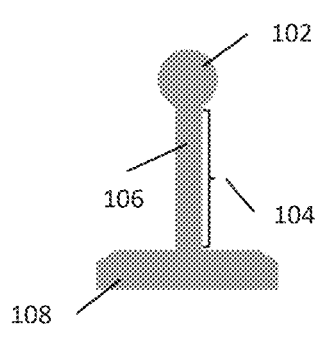
FIG. 10A depicts an exemplary master mold for the fabrication of the tissue support member.

The shape of the mold is customizable and designed based upon the shape of the required tissues and/or organoids. In an embodiment, there is provided a mold comprising a generally spherical portion together with an elongate portion that is attachable to the sphere shaped portion, which is particularly suited for the preparation of cardiac organoid chambers. FIG. 10A illustrates an example of a SLA printed mold with egg-shaped head. The egg-shaped resin mold 100 includes the following portions: head 102, neck 104, fillet 106; and a platform for casting 108.

The 3D printer allows the user to alter the shape of the mold easily by adjusting a CAD file (e.g. created with Autodesk Fusion 360), printing a new template, and casting from this to mimic the shape. The tissue support will assume this shape when the interior of the polymeric lining is filled with the volume of solution it was originally drawn to hold.

Figure 10B:
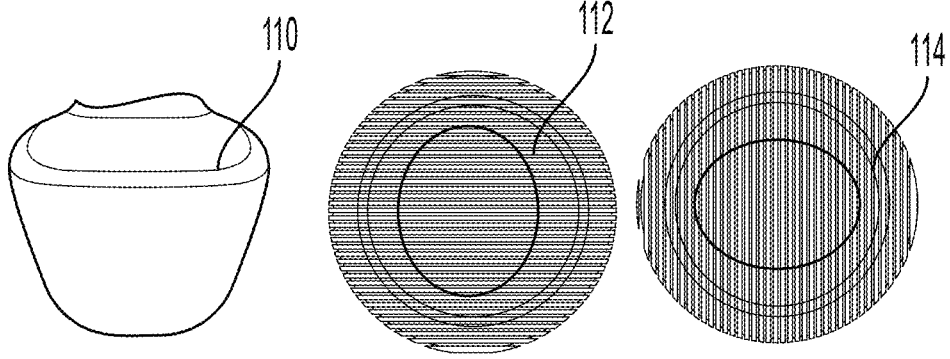
FIG. 10B depicts configurations of an exemplary head portion of a mold, in a general heart ventricle shape in spherical form and patterned with horizontal or vertical grooves for inducing cell alignment in the organoid.

Advantageously, the mold is configured with a heart ventricle shape 110 as depicted in FIG. 10B, which may be derived from 3D medical imaging techniques, e.g. MRI, to allow the preparation of a 3D heart. Optionally, the external surface of the mold comprises one or more topological features, such as horizontal grooves 112 or vertical grooves 114 as depicted in FIG. 10B, to enable the preparation of tissue support with the topological features for inducing cell alignment upon tissue compaction thereon.

In an embodiment, a SLA printer (Form 3, black resin, FormLabs) can be used in printing the mold. The resolution of this type of printer is 25 microns, making it possible to achieve a smooth surface on the molds, crucial for release of thin layers of undamaged polymeric material. Optionally, acetone vapor treatment can be used for further smoothing of plastic mold surfaces.

Figure 10C:
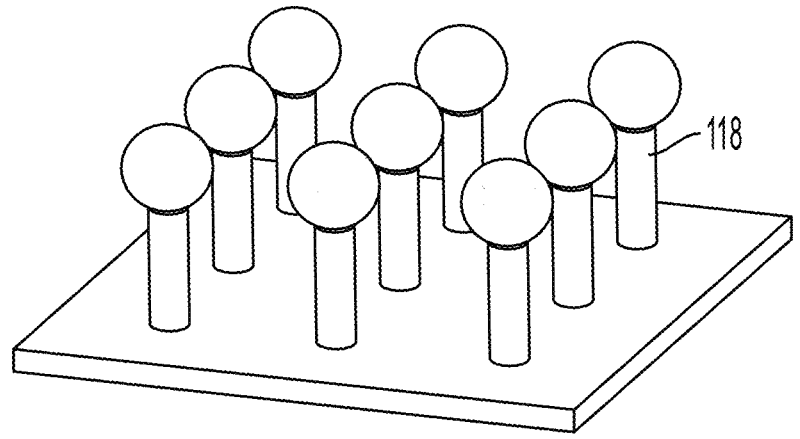
FIG. 10C depicts a master mold array for the fabrication of exemplary multiple tissue support members according to an embodiment of the present disclosure.

Advantageously, the fabrication method is a completely or semi-automated, high throughput process, involving an automated casting step, which is expected to improve uniformity and at the same time allow scalability for large scale commercial production. FIG. 10C depicts a master mold array 118 that can be used for mass production or high throughput applications so as to increase the efficiency by fabricating multiple balloons (equivalent to the handling of cells in a 96-well plate).

An exemplary process for organoid tissue fabrication using the permanent indwelling balloon according to an embodiment of the present disclosure is depicted in FIG. 11A. In this example, a mold 200 with an ellipsoid-shaped head is printed using SLA technology, and polymer 202 was deposited on the top of the mold, allowing the formation of a thin and soft polymeric tissue support 205 having a balloon-shaped head and an elongated body following curing. The tissue support is attached to a cannula 208 loaded with water for tissue 210 formation.

In a preferred embodiment of the present disclosure, the issue support is prepared by drop-casting the selected polymer on the mold as depicted in FIG. 11B. In an embodiment, a paintbrush is used to coat the neck portion 104 of the mold before drop-casting the polymer on the top of the head portion 102.

Figure 12B:
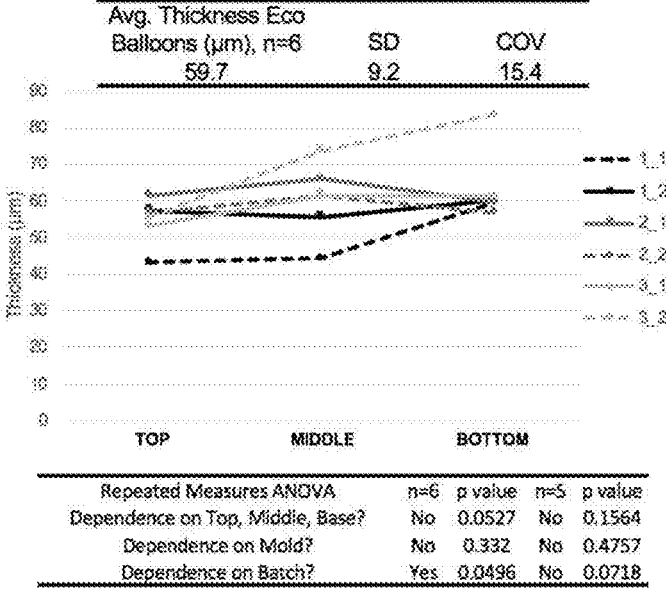
FIG. 12B depicts the variation across the top, middle, and bottom of the balloon.

The tissue support prepared by drop-casting method according to the present invention demonstrate great consistency across different fabrication batches and using different molds. As further described in the examples, the tissue supports formed are measured using a method depicted in FIG. 12A, whereby the resilient member 500 of the support is dissected and a slice of the member is imaged on its side, allowing for measurement of the thickness in ImageJ. FIG. 12B illustrates the measurements taken across the top, the middle, and the bottom of the balloon section.

Measurements were taken for four balloons that are fabricated with variations to the drop-cast protocol as summarized in Table 5. The cross-sectional area of the balloon portion of the tissue support as a function of loading volume is provided in FIG. 13. The observed uniformity under loading demonstrates that the resulting balloons are fairly insensitive to variations in fabrication protocol.

Figure 14A:
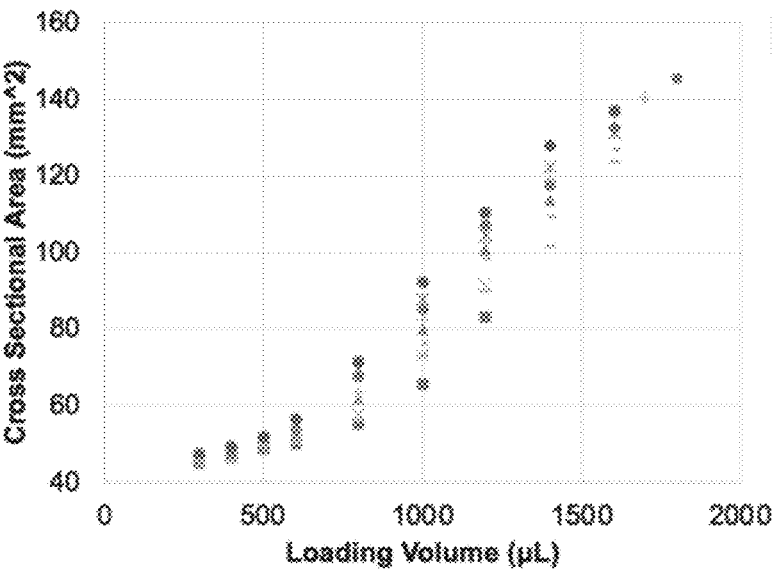
FIG. 14A depicts the cross-sectional areas of an exemplary inflated tissue support member based upon various loading volumes.
Figure 14B:
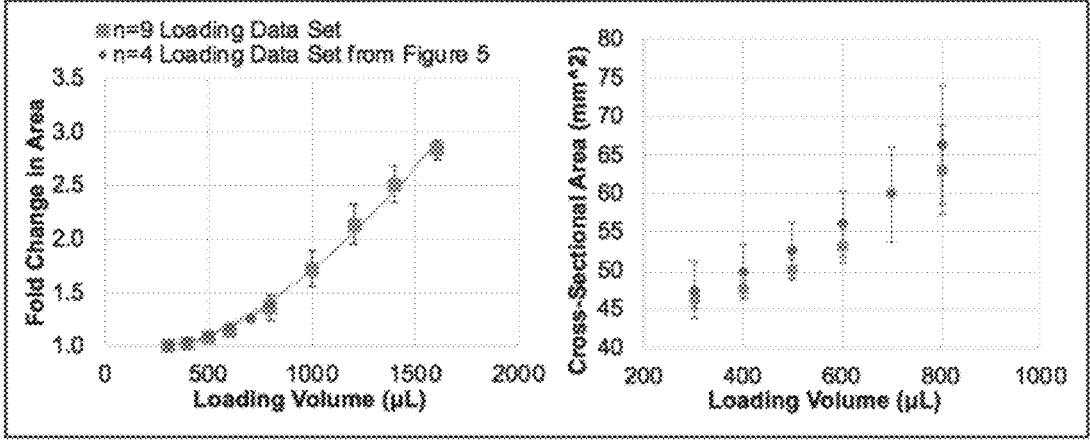
FIG. 14B depicts expansion of the inflated tissue support member as a function of loading volume. The right hand plot is a zoomed in view of the data on the left. Error bars shown are for standard deviation.
Figure 14C:
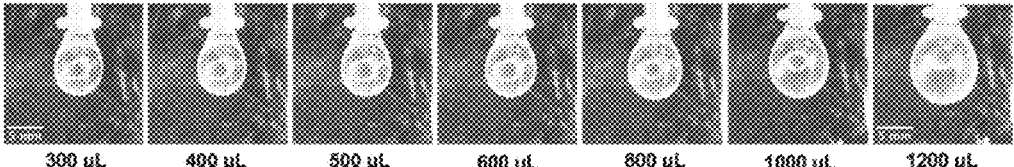
FIG. 14C depicts images of the tissue support member inflated with various volumes of liquid.

To further illustrate the consistency across balloons fabricated using different drop-casting method and molds, three different batches of four balloons each were made using a set of 4 molds. Three out of four of the balloons were used for testing by measuring cross-sectional area as a function of loading volume (300-1600 µL). The changes in cross-sectional area with an increase in loading volume that were tested are illustrated in FIG. 14A. Both data sets for expansion as a function of loading volume as depicted in FIG. 14B show good correlation across batches and molds. Cross-sectional area images showing the expansion of the exemplary balloon are depicted in FIG. 14C.

Figure 15A:
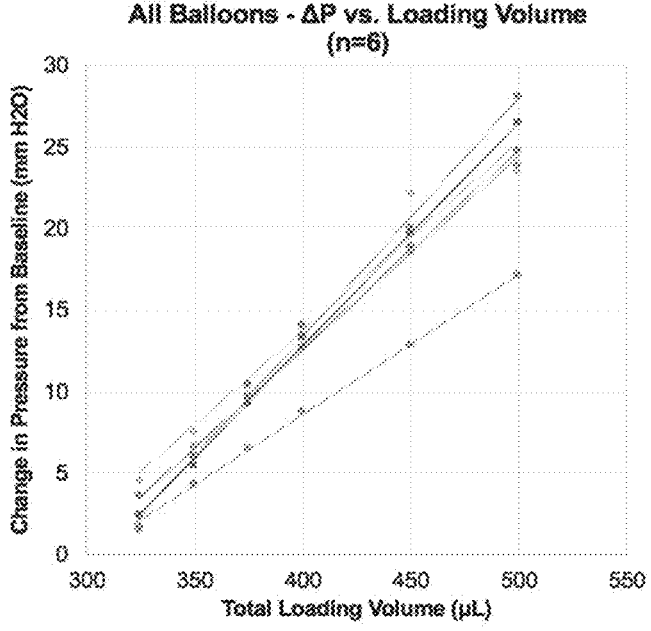
FIG. 15A depicts the changes in pressure with increased loading volume of the tissue support members of various fabrication batches made from various molds.
Figure 15B:
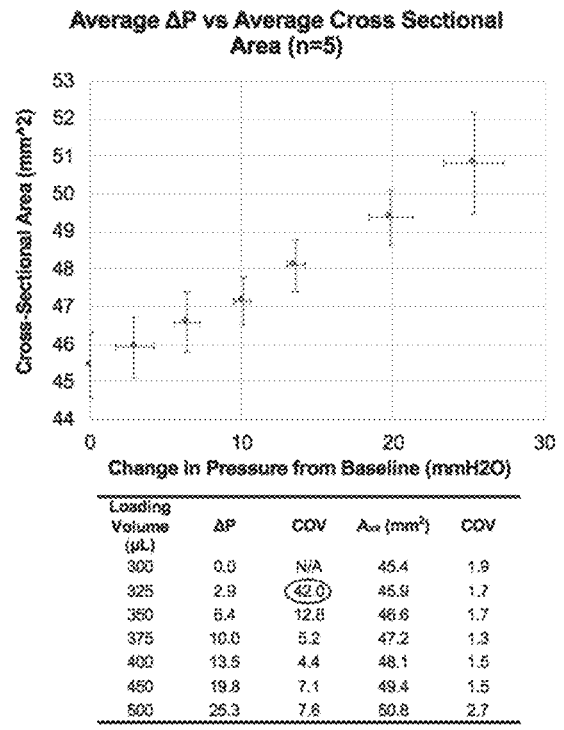
FIG. 15B depicts cross-sectional area as a function of change in pressure from baseline. The table documents the coefficients of variation at the various loading volumes and error bars show standard deviation.

FIG. 15A further shows that the changes in pressure with increased loading volume are consistent across fabrication batches and molds. FIG. 15B, which illustrates the cross-sectional area as a function of change in pressure from baseline, is shown for all data in FIG. 15A minus the leaking balloon. The table documents the coefficients of variation at the various loading volumes. Error bars shown are for standard deviation. The results demonstrate that the method of the present disclosure provides fabrication repeatability, as seen by the similar response curves across multiple batches and molds.

EXAMPLES

Example 1: Biological Preparation of Tissue

Cardiomyocyte Preparation

Human pluripotent stem cells (hPSC) were differentiated into human ventricular-like cardiomyocytes (hvCMs) following a proprietary protocol involving small molecule-based directed differentiation using the embryoid body method [10]. In brief, cells were maintained on Matrigel coated plates with mTeSR1 at 37° C. with 5% $CO_2$. On the first day of differentiation, cells were digested to form small cell clusters suspended in mTeSR1 with Matrigel, 1 ng/ml bone morphogenetic protein 4 (BMP4) and 10 µM ROCK inhibitor Y-27632 (RI) for 24 hours in an ultra-low attachment plate under hypoxic conditions. Medium was then replaced with StemPro-34 medium with GlutaMAX supplemented with 50 µg/mL ascorbic acid, 10 ng/mL activin A, 10 ng/mL BMP4, and 5 µM RI. After 3 days, cells were cultured in StemPro-34 medium supplemented with 50 µg/mL ascorbic acid and 5 µM IWR-1 for 4 days, when spontaneously contracting cardiomyocytes became evident. Afterwards, beating cardiomyocyte cell clusters were maintained in RPMI 1640 supplemented with B27 and 50 μg/mL ascorbic acid in normoxic condition. Batches were assessed with flow cytometry on differentiation day 13 or 14 for cardiac troponin T-positive cells, with a quality control criterion of at least 60% cTnT+ cells.

Preparation of Cell Solution and Seeding

Cardiospheres of spontaneously beating human ventricular-like cardiomyocytes (hvCMs) were dissociated on day 15 using 0.025% trypsin-EDTA (TE) and allowed to reaggregate in suspension in RPMI+B27 supplement (with Ascorbic Acid and ROCK inhibitors) for 72 hours prior to the day of seeding. Each human ventricular cardiac organoid chamber (hvCOC) required $1 \times 10^7$ hPSC-CMs. Human foreskin fibroblasts (HFF) were harvested from the culture plate using 0.05% TE. Each hvCOC also required $1 \times 10^6$ fibroblasts. The cellular mixture was formed by combining the hvCMs and HFF cells with the following components: 40% of 5 mg/ml collagen, 1.5% 1M NaOH, 9% 10×MEM, 12.5% 0.2M HEPES, 10% DMEM with Newborn Calf Serum (NCS, 10%) and 6-10% Matrigel, then replenished by ultrapure water to 100%. The total volume was brought up to 1650 μL per hvCOC using NCS media.

Mold and Bioreactor Preparation

To prepare the balloon, the neck of the balloon was rolled onto the fluid loading port, positioning the head just below the end of the port as seen in FIG. 4D. Using a severed 1 mL pipette tip, an O-ring (5.8 mm) was stretched and then rolled into place on the attachment/loading hardware 3 mm above the base to hold and seal the balloon in place. A porous ring was placed just below the O-ring to enhance tissue attachment. The balloon was filled with the appropriate volume of distilled water (230 μL) to form its original shape. The balloon and attachment tubing were fit into the lid of the bioreactor vial. This entire setup was sterilized using a CoolClave UV ozone sterilizer (Genlantis) for 1 hour. It was confirmed that UV treatment did not affect balloon stiffness as shown by similar expansion response to loading before and after sterilization (data not shown).

On the day of tissue formation, a hydrogel was dissolved in PBS in a microwave. The hydrogel solution was poured into the bioreactor vessel and a mold was inserted into the top to form a pocket as the solution gels. The mold was pulled out carefully. Two mL of 2% BSA solution was added into the agarose mold, incubated for 1 hour before aspirating the BSA and washing with PBS once. The balloon attached to the lid was inserted into the hydrogel mold; the position was adjusted to visually ensure equal distance from all sides. The mold was air dried in the hood before the cell mixture solution was added to the space between the agarose mold and balloon. The bioreactor was incubated for 2 hours for gel solidification before being topped off with 8 mL NCS medium to reach the top of the bioreactor. Medium was changed every 24 hours while the organoid was compacting; the medium change was performed every other day after the organoid was removed from the agarose gel until the day of the experiment. The hvCOC chamber compacted around the balloon and was ready for experiments by Day 10 postfabrication.

Example 2: Biological Observations and Experiments Using Tissue Support

Ability to Form Tissue Compacted Around Balloon

A camera along with a thresholding interface was used to monitor the changes in cross-sectional area of the tissue which was used to approximate changes in volume. A pressure catheter (SPR 524, ADI and Millar) was inserted through the tubing to the inside of the balloon in measure the changes in pressure.

It was observed that the tissue infiltrates the porous polyethylene ring and forms a tight interface with the balloon surface. As seen in FIG. 5, for changes in internal volume (inflation and deflation), the tissue appears to track with the balloon surface. Maintaining an interface is necessary to keep pressure-volume measurements consistent across the experiment. The tissue setup does not leak as evident by the ability to hold a constant internal pressure when the tissue is hydrostatically loaded using the attachment tubing, as shown in FIG. 2B where the measured applied loading pressures were stable throughout each measurement.

The balloon allows the inversion of the COC tissue during compaction, resulting in more uniform tissue fabrication. Furthermore, the balloon is compatible with a syringe pump for oscillated loading of the chamber during culture, allowing the option of mechanical stimulation.

A separate experiment was also conducted to confirm that balloons without tissues do not leak over time upon loading with fluids, as the measured pressures were found to be stable over a time period for 5 minutes, as shown in Table 3 below:

TABLE 3

| Loading Volume (μL) | Change in Pressure Reading from Baseline (mmH$_2$O) | $p_{initial} = p_{final}$ (5 minutes)? |
|---|---|---|
| 300 (Baseline) | 0 | Yes |
| 500 | 20 | Yes |
| 700 | 41 | Yes |
| 900 | 50 | Yes |
| 1100 | 50 | Yes |
| 1600 | 50 | Yes |

The formed tissue was healthy and remained viable for up to 30 days on the balloon. Tissue contraction was strong enough to visibly compact the balloon during beating, causing a measurable change in cross-sectional area and internal pressure. These results demonstrate that the balloon is a biocompatible construct that prevents leakage and does not affect the ability to measure pressure-volume relationships of the hvCOC, allowing functional testing of cardiac organoid chambers.

For preliminary biological validation, tissues fabricated with the indwelling balloon were compared to tissues fabricated using the traditional method with the catheter withdrawn. During these tests, balloons were being made with polymeric material Ecoflex with a silicone filler, MicroLubrol 200 Fluid Pure Silicone Oil Polydimethylsiloxane (PDMS) 100 centistokes (cst) viscosity). In this experiment, one tissue was fabricated with each method. PV measurements were taken on days 10, 11, and 12 with hydrostatic pressure loading at 0, 5, and 10 mmH$_2$O. PV loops obtained from the indwelling balloon hvCOC preparation were comparable in shape to those using the catheter-based hvCOC on day 10; however, while consecutive loops drifted for the catheter preparation, the balloon loops more consistently overlapped. These results show that tissues' responses to loading did not change over time, indicating that the tissues formed using the tissue support of the present disclosure are more stable and durable.

The real benefit of the balloon in this experiment was seen when testing the tissue chambers over time as the indwelling balloon hvCOC preparation proved to be more stable and consistent with repeated measurements. The catheter preparation began to compact on itself over time after the catheter was removed (FIG. 2A), and was unable to maintain pressure loading (FIG. 2B) or generate PV data (FIG. 2C) by the end of the experiment. The indwelling balloon hvCOC preparation had consistent shape (FIG. 2A), maintained the applied pressure loading (FIG. 10B), and generated PV loops at 5 mmH$_2$O loading pressure for all three days of testing (FIG. 10C). It is surprising that the PV stability is significantly improved for tissues made with the tissue support of the present disclosure.

In FIG. 2C, the result obtained at D11 for the traditional catheter is faded as the tissue was unable to hold the load on this day; therefore, the PV loop is not an accurate representation under this load. While there is a slight decrease in response from the tissue fabricated with the tissue support of the present disclosure on D12, the traditional catheter could not even be measured on this day. Similar experiments to this continued to show the hvCOCs with indwelling balloons to be as clean signal-wise and more durable experiment-wise when compared to the previous catheter-based hvCOC preparations.

Figure 16A:
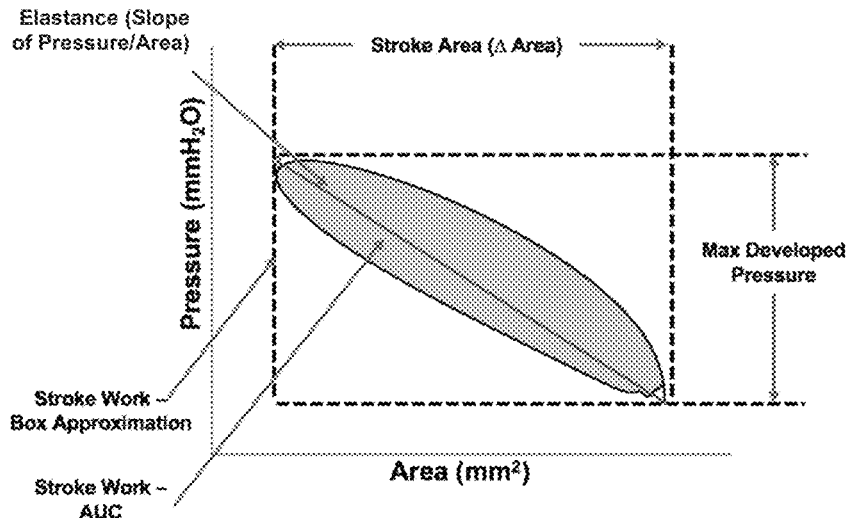
FIG. 16A depicts how cardiac parameters are calculated from the PV loop data collected during hvCOC acquisition.
Figure 16B:
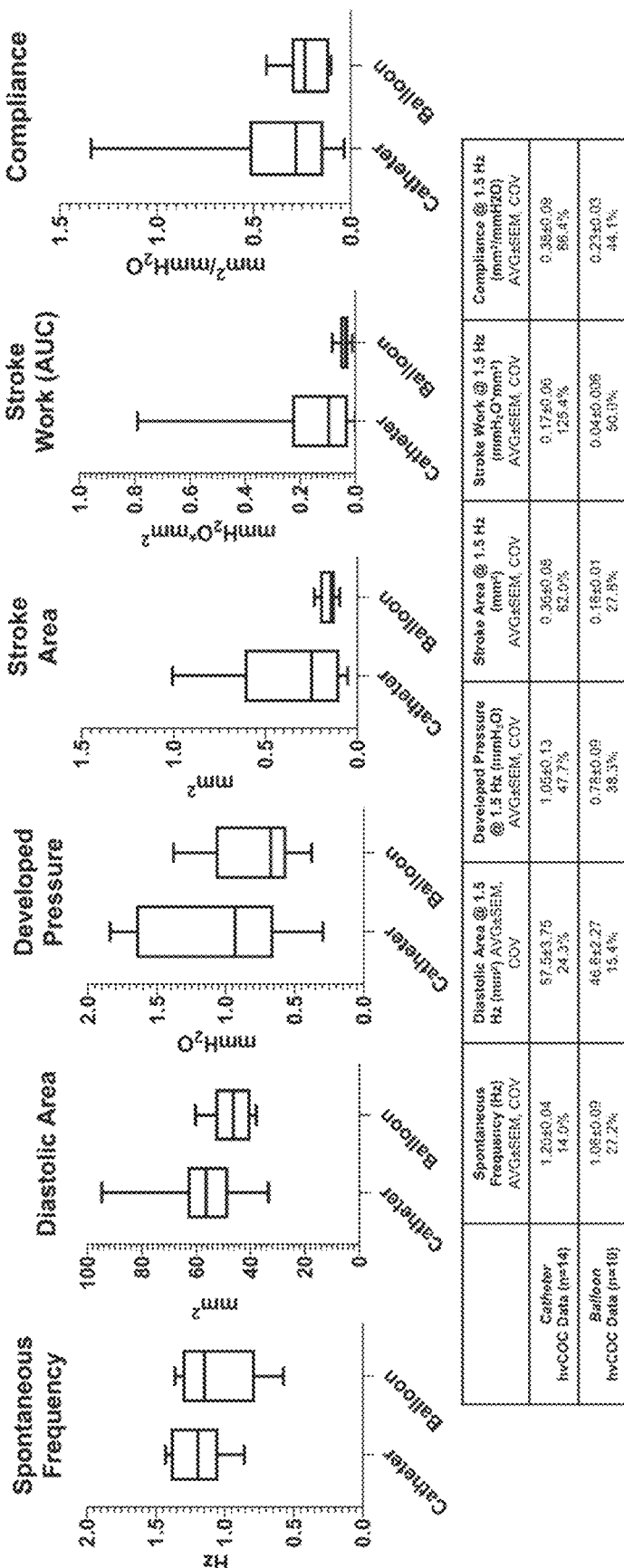
FIG. 16B depicts a comparison of the variation in experimental parameters for hvCOCs made with the catheter method (n=14) to hvCOCs made with the balloon method (n=10). Plots show mean value±SEM. Table shows mean, SEM and COV for the catheter- and balloon-based hvCOCs.

The indwelling balloon reduces variation of hvCOC properties, including initial size, developed pressure, and stroke area, such that a more consistent baseline can be established for drug testing and disease modeling. With an established protocol for the balloon tissue fabrication, the variability of the system was tested across n=10 balloon hvCOCs fabricated according to the methods described herein. On day 10, tissues were measured at baseline (ambient pressure loading) while being paced at a physiologic rate of 1.5 Hz (90 bpm). Pressure and volume (PV) data were collected for 30 seconds during pacing for each tissue. In house software was used to calculate maximum developed pressure, stroke area, and stroke work from resulting PV loops. Cardiac troponin percentage of the starting cell population, the diastolic area, and spontaneous beat rate of the hvCOC were also recorded and used for analysis. The coefficient of variation (COV) and standard error of the mean (SEM) were calculated for various properties of these 10 tissues and compared to the n=14 hvCOCs fabricated with the former catheter-based method in a previous study.[14] FIG. 16A shows spontaneous frequency, diastolic area, developed pressure, stroke area, stroke work (AUC), and compliance data for catheter- and balloon-hvCOCs. In the table below, the COV and SEM for the two groups are compared. Both the COVs and SEMs for balloon-hvCOCs are less than that of the catheter fabrication across all parameters except spontaneous beat rate, with the greatest reductions in variability noted for the stroke area, stroke work, and chamber compliance.

In addition, spontaneous beat frequency, the stroke work (box approximation), and compliance were plotted as functions of percent of troponin-positive cells (% CTNT), showing clear trends for the balloon hvCOCs. Data points of hvCOCs fabricated from the same cellular batch are plotted in the same color. Batches were ranked in order of % CTNT+ such that in both studies the colors go in the same order of increasing CTNT; however, batches were not the same across the two fabrication methods. In comparing batch-to-batch variation in hvCOC performance, based on batch-dependent differences in cardiomyocyte differentiation efficiency, balloon hvCOCs tend to show less intra-batch variability and stronger overall dependence on cardiomyocyte content, suggesting that variation in the data is more a function of cellular composition and less a function of fabrication method, in contrast to the catheter hvCOC data. Using linear regression analysis, the balloon hvCOCs which have higher R$^2$ values and statistically significant slopes, reveal an expected dependence on cardiomyocyte concentration (represented as % CTNT+), whereas this dependency is masked by the high variability and poor correlation in the catheter-based hvCOC. hvCOCs made from batches of cells with comparable myocyte composition should exhibit similar baseline properties. The variability in catheter hvCOCs fabricated from cell batches with similar % CTNT+ makes it difficult to compare to a baseline when diseased states and drug concentrations are introduced. Because the balloon reduces variation due to fabrication, it has been used by the inventors for both disease models and drug toxicity studies.

Measurement of Tissue Across Multiple Days

Tissues fabricated using a single layer balloon were compared to tissues fabricated using a double layer balloon. In the study presented here, tissues formed on 2 single layer balloons (Ecoflex only) and 2 double layers balloons (Ecoflex+silicone filler) were tested over 5 days in culture. From the pressure-volume loops, it is evident that there is enhanced performance, size maintenance, and stability in the formulation prepared with the single layer balloons across all days in culture. FIG. 6 shows the pressure-volume data for all four preparations.

Loading Tissue with Balloon Construct in Place

Loading the tissue by stretching the chamber is a needed step during experiments to examine the well-known Frank-Starling property of the heart, by which the heart beats more strongly with increased load. In the past, hydrostatically loading the tissue was made difficult by leakage of the hvCOC; as the load increased, the increased pressure would force liquid through the permeable chamber wall. In order to counteract this leakage, each cannula attached to an organoid had to be connected to a large reservoir of liquid whose height could be adjusted. This required complex setup and could only be used for a single experiment, as the detachment of the setup creates uncontrolled pressure changes that often destroy the delicate hvCOC tissue.

With the permanent balloon of the present disclosure creating a leak-proof impermeable barrier, hydrostatic loading can be done directly in the attachment tubing by adding controlled volumes of liquid without requiring a large fluid reservoir. This means that loading can be repeated on different experimental days without destroying the hvCOC tissue, and can easily be applied for extended periods of time inside the incubator to satisfy different experimental conditions.

In cardiac tissue, increased load on the tissue should result in enhanced contraction strength, resulting in greater developed pressure and stroke area according to the Frank-Starling mechanism. In the plots below, the effects of loading on these parameters can be seen in the hvCOC preparation with indwelling Eco balloon.

First, the plots in FIG. 7 show that as liquid is added to and removed from the attachment tubing, both the diastolic area and the diastolic pressure increase and decrease as expected (except for diastolic area, loading volume of 50 µl). To see how this affects the tissue response, the normalized developed pressure, stroke area, and stroke work were plotted in FIG. 8. The increase in developed pressure up to 200 µl of loading suggests enhanced contraction, consistent with a functional Frank-Starling mechanism in the hvCOC.

The decrease of developed pressure over 200 µl and loss of contraction signal over 300 µl indicates potential damage at the highest loading condition, so that optimal loading is within 200 μl of added volume. The decrease in stroke area prior to 100 μl suggests that optimal loading may even be less than 150 μl.

Shielding Effect of Silicone Balloon

A common practice with engineered cardiac tissues is the use of stimulation to pace tissues at different frequencies. This technique often involves field stimulation, triggering a voltage across two electrodes in media solution to create an electric field, which in turn applies current uniformly across the tissue. However, this electric field can damage or interfere with signal from sensing equipment. It is of interest to incorporate a PV catheter (PVR-1030, ADI MPVS equipment) for measurement of the hvCOC preparations, however, such an experimental setup has the above risks when using it in the presence of an electric field.

To test if the balloon offers a shielding effect from the electric field and would allow us to use the PV catheter inside the balloon while there is an electric field outside stimulating the tissue, we conducted the experiment diagrammed in FIG. 9. An oscilloscope was used to measure the voltage profile for 5V, 10 ms biphasic stimulation both inside and outside the balloon. As seen in the different voltage profiles measured, it is observed that shielding effect is provided by the balloon. In other words, the tissue member may provide an insulating layer that can shield the inside environment from the surroundings.

Example 3: Fabrication of Tissue Support

A master mold on which the balloon can be cured was used to prepare the tissue support. The mold for the silicone balloon consists of 2 parts: the head and the neck. The head is used to control size and shape of the balloon and therefore the tissue, and the neck is used for creating a sleeve that allows for attachment to different hardware components. These molds were 3D printed using an SLA printer (Form 3, black resin, FormLabs).

In this experiment, an egg-shaped, ~230 μL, mold was used to best mimic the catheter size and shape. In this design, a fillet was used to connect the neck and the balloon as to provide easier release after curing of the polymer; the neck is sized to match the diameter of the attachment hardware used during tissue measurement.

Once printed, the master molds were silanized to minimize adhesion as follows; operating within a chemical fume hood, each mold was UVO treated for 30 minutes using a JetLight Sterilizer before being placed in a desiccator with a few drops of trichloro(1H, 1H, 2H, 2H-perfluorooctyl) silane (Sigma Aldrich) placed on a glass slide. The desiccator was put under vacuum and allowed to sit overnight. When molds were ready for use, they were positioned with the neck at the base and the head at the top; a support structure to hold molds upright can be 3D printed along with the balloon mold as shown in FIG. 10.

EcoFlex is mixed in a 1:1 ratio of components A:B as instructed by the material manufacturer. After mixing, a paint brush was used to apply EcoFlex to the neck of the balloon to enhance the flow of the material down the sides of the mold during the drop-casting process. A plastic Pasteur pipette or dropper was used to deposit 500 μL of EcoFlex onto the top of the mold. To get even distribution while depositing manually, a small circular motion was used during deposition and then deposition was finished with the tip of the dropper in the center top part of the mold.

The approximate calculation for achieved thickness of the resulting shell ($h_a$) is dependent on the viscosity ($\mu_o$), density ($\rho$), and curing time ($\Sigma_C$) of the material as well as the radius (R) of the mold head. By applying the material immediately to the 3D printed mold after mixing (thereby maximizing the curing time), very thin and uniform layers are achievable. The ability to create these balloons via this method allows for a very simple and scalable fabrication procedure that results in fairly uniform results that are less sensitive to parameters that are not tightly controlled. The following approximation [14] results in a cast balloon wall thickness that is on the order of magnitude of the target thickness (Eq. 6).

$$h_a \sim \frac{\sqrt{\mu_0 R}}{\rho g \tau_C} \qquad \text{Eq. 6}$$

TABLE 4

| Thickness ($h_a$) | 34 | μm |
|---|---|---|
| Viscosity ($\mu_0$) | 3 | kg/m/s |
| Radius of Mold (R) | 0.0034 | m |
| Density ($\rho$) | 1000 | kg/m³ |
| Gravitational constant (g) | 9.8 | m/s² |
| Curing Time ($\tau_C$) | 900 | s |

The EcoFlex solution was allowed to flow down the sides of the balloon mold for 45 minutes (pot life of the polymer). Right before heat curing in an oven, a pipette tip was used to loosen the polymer at the base of the neck, allowing trapped air to easily escape to reduce bubble imperfections during heat treatment. The mold with polymer was baked at 100° C. for 30 minutes before removal to cool at room temperature. Multiple layers can be added to increase thickness and/or durability of the balloon by repeating the above process prior to balloon removal from the master mold.

It was observed that the fabrication protocol for single layer balloon had high yield and consistency, with minimal thickness (60 μm) as shown in the Thickness and Yield section to follow. During fabrication trials below, wait time and bake time varied between 30-45 minutes as we explored different protocols but were consistent within an experiment when comparing batch-to-batch consistency (unless otherwise specified). As indicated in the drop-cast formula (Eq. 6), these values in conjunction with the material used can be tailored to create different thickness balloons.

For balloon removal from the mold, excess material was cut away from the base of the mold with a razor blade. Then gently, starting at the base of the neck, the cured polymer sleeve was rolled back from the neck and over the head shape such that the balloon was inside out. Balloons were then reversed so the smooth outer surface is again on the outside. Balloons were sterilized by storing in 70% ethanol until needed for organoid tissue fabrication.

Example 4: Mechanical Testing and Confirmation of Consistency

Several different types of testing have been performed to confirm consistency of balloons across different fabrication batches and using different molds; these methods are described below but all indicate that fabrication of balloons is consistent. All mechanical testing work is shown for EcoFlex only (Eco) material.

Thickness and Yield

Three different batches of four balloons each were made using a set of four master molds. These balloons were then removed and filled with water to test for leaks, with a balloon passing the yield test if it didn't leak. The yield for this particular experiment was 11 out of 12, which is over 90%. Two out of four from each batch were then dissected into their top, middle, and bottom sections. Slivers of material were put on their side and imaged to get a cross-sectional picture that was used to quantify thickness in ImageJ; this was done by hand using the length tool with each image being measured in three locations across the strip.

Balloon thickness was relatively uniform across top, middle, bottom and between the batches, as seen by the plots and variation shown in FIG. 12, resulting in an overall coefficient of variation of 15.4%. A repeated measures ANOVA test was performed to determine the differences across (1) balloons' top, middle, and base, (2) within a batch, and (3) across batches. The results when all data is included are shown in FIG. 12. When the outlier (sample 3_2) is removed, there is no significant difference between any of the parameters.

Fabrication Method Effect on Thickness and Expansion

To test the robustness of the fabrication process and sensitivity to variations in protocol, four different balloons were created with the goal of varying the thickness by changing steps in the protocol.

The thickness was measured at top, middle, and bottom as above, and the average values compared (see Table 5). An unpaired standard t-test was used to compare the average thickness values across the three varied protocols to the control protocol; no average thickness was significantly different than the control ($p > 0.05$ for all t-tests).

Figure 13:
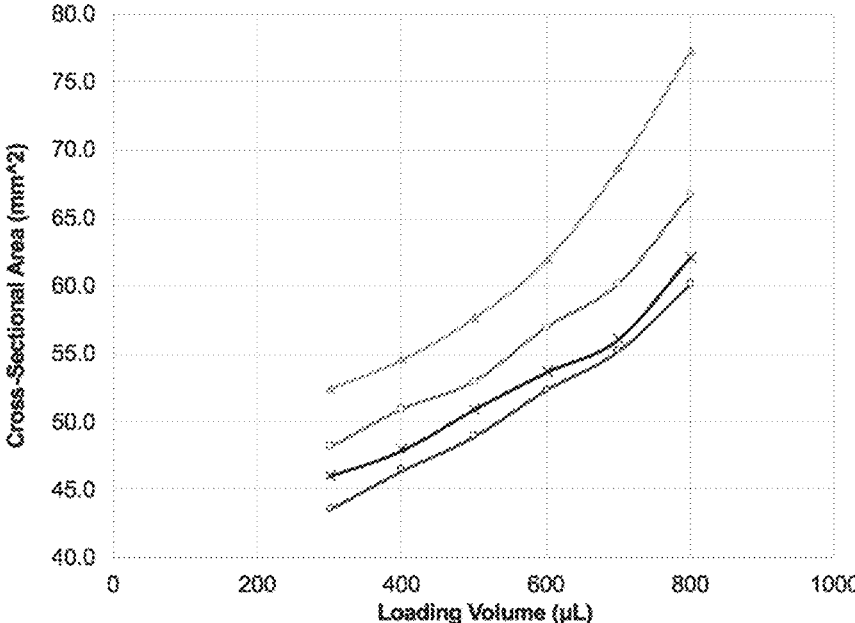
FIG. 13 depicts the cross-sectional area as a function of loading volume for exemplary embodiments of four tissue support members (in this case balloons) fabricated with variations to the drop-casting protocol.
Figure 19:
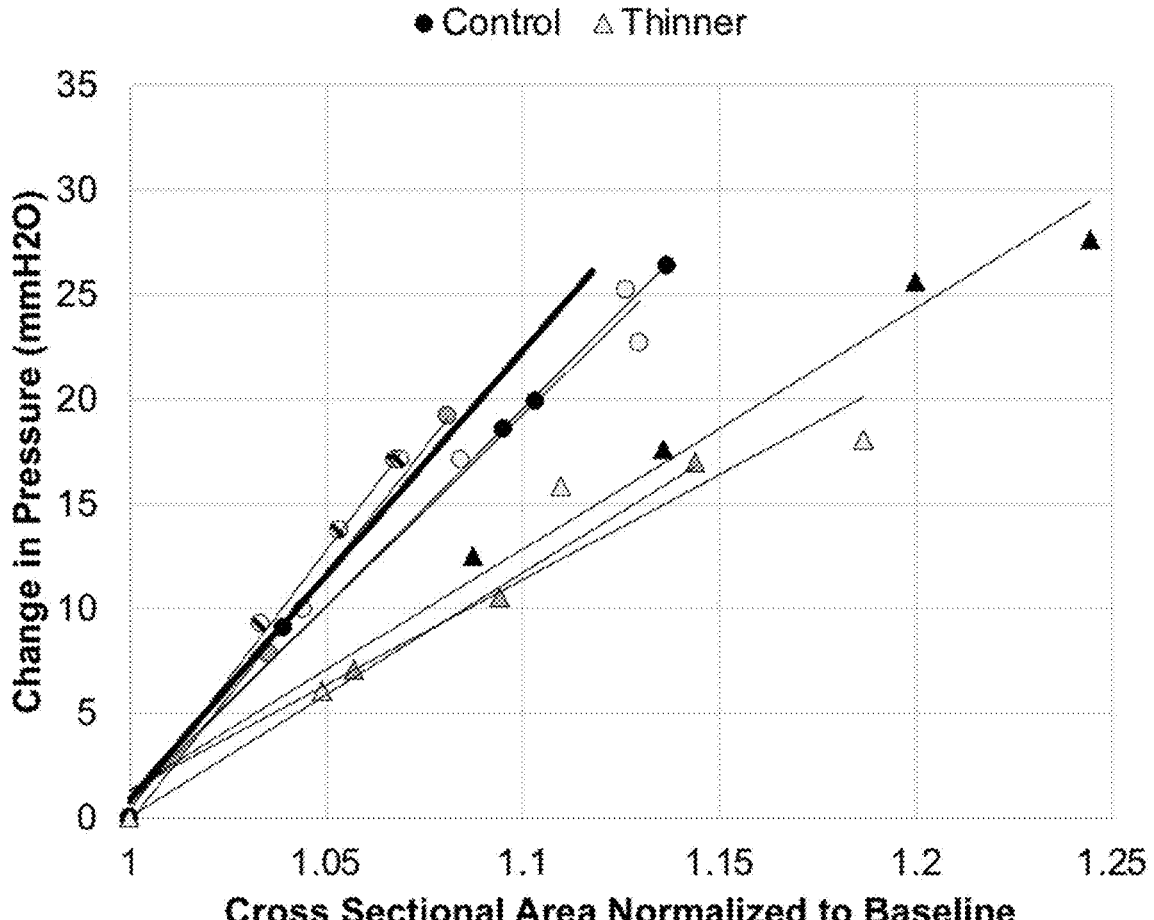
FIG. 19 depicts a response plot of Change in Pressure vs. Change in Cross Sectional Area.

An one way ANOVA was used to compare the thicknesses across the top, middle, and base of each protocol's balloon (n=1); there was only a significant difference for fabrication method three which had a 20 minute pre-cure, resulting in a much thicker base. Balloons were then loaded with volumes of distilled water using a syringe, starting at a volume of 300 μL up to 800 μL. Images of the cross section were taken at each loading volume and the cross-sectional areas of the balloons were measured in ImageJ using the oval tool to define the area by hand and plotted as a function of loading volume. Despite inconsistency between initial cross-sectional area measurements, the curvature of the increase in volume as depicted in FIG. 13 suggests the balloons are responding similarly. The limited variability suggests that expected deviations in fabrication (which should be much less than the intentional ones presented here) should not cause noticeable variation in the resulting balloons.

retesting and showed same response as before incubation, suggesting the mechanical properties were not changing over time in culture (FIG. 19).

Expansion Uniformity—Measured Cross-Sectional Area vs. Loading Volume

To ensure that the fabrication protocol was uniform across different batches of material, three different batches of four balloons each were made using a set of four molds, all of which bearing the same geometry as the master mold. Three out of four of the balloons were used for testing measured cross-sectional area as a function of loading volume (300-1600 μL).

All data points were plotted below in FIG. 14A, showing good overlap of all nine samples. At a certain point, the volume added approached the top of the loading port; at this point, if solution was added slowly, the balloon continued to expand to account for the added volume. In FIG. 14B, the average expansion as a function of loading volume is shown; this is compared to the average data from the previous experiment plotted in FIG. 13, showing the consistency in loading response between the two data sets. FIG. 14C shows an example response of a balloon to loading.

Loading Uniformity—Change in Pressure vs. Loading Volume

It is of interest to be able to load the tissue chambers and to understand what amount of strain this puts on the tissue. Ideally, the balloon system allows each tissue to be loaded consistently with a set volume being added to the fluid loading port. In order to understand the effects of loading volume on internal pressure and how that relates to expansion, an experiment on balloon consistency across batches was performed.

Six balloons across three batches were compared by loading with volumes from 300-500 μL (in smaller volume increments as this had been determined to be the target region for loading biological tissues); for this experiment, a micro-pipettor attached to a stiff, thin piece of tubing was used to more accurately deliver liquid to the chamber. The change in pressure inside the chamber as well as the cross-sectional area were measured at each loading volume. All change in pressure vs. loading volume data for the six balloons is shown in FIG. 15A. FIG. 15B shows cross-sectional area vs. change in pressure for five balloons (eliminating one balloon with a documented leak as evident by the line deviating from the trend in FIG. 15A).

The coefficient of variation at each loading volume for both change in pressure with change in area are shown in the

TABLE 5

| Fabrication Method | Avg. (μm) | SD (μm) | COV (%) | Notes |
|---|---|---|---|---|
| 1 Normal Fabrication | 61.2 | 8.6 | 14.0 | N/A |
| 2 Wait 10 minutes before depositing EcoFlex | 62.5 | 10.7 | 17.1 | Some insensitivity to first additional curing time prior to deposition, greater |
| 3 Wait 20 minutes before depositing EcoFlex | 67.5 | 12.7 | 18.8 | thickness variation from top to bottom |
| 4 3 consecutive depositions of EcoFlex | 60.0 | 7.8 | 13.0 | Insensitive to amount of material deposited on the top |

In an additional experiment, 10% by weight of a commercial thinning agent (SmoothOn Silicone Thinner) to the standard EcoFlex 00-30 formulation of 1A:1B and following the same casting procedure described above, balloons were fabricated that were ~10 microns less than the controls. They also had greater expansion per additional hydrostatic load). The balloons were put in culture for 16 days prior to table in FIG. 15B. The largest variation was seen for the change in pressure for the initial loading step of 25 μL. Other than this deviation, the plots below demonstrate uniformity in the change in pressure and change in cross-sectional area. Based on this mechanical testing, the responses of the balloons across different batches and different molds are consistent and the variation is less than the anticipated variation across biological samples. It is therefore expected that the balloons can help to standardize the measurement platform across tissue samples.

Example 5. Indwelling Balloon Validation

Figure 17A:
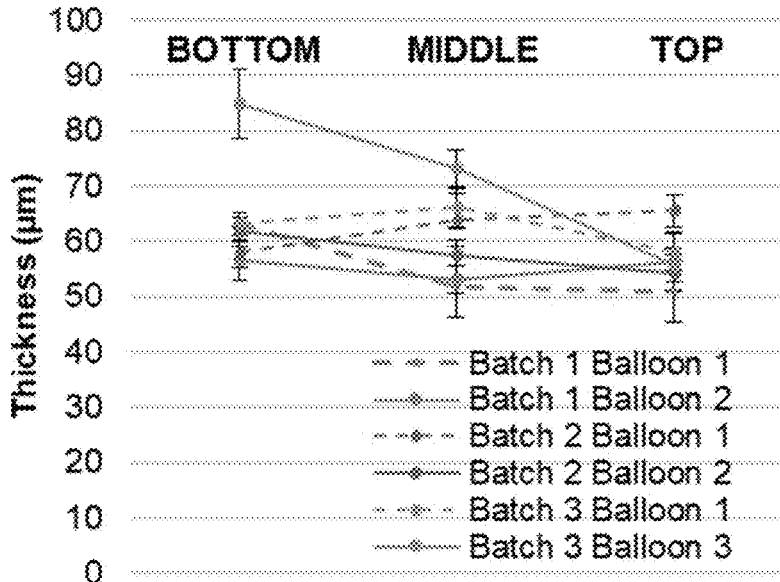
FIG. 17A depicts a method for measuring regional thickness of cast elastomer balloons. Plot shows variation across top, middle, and bottom of the balloon. Error bars represent standard deviation for n=3 measurements per slice of material.

To study consistency in balloon membrane thickness, three different batches of four balloons each were made using a set of four master molds. These balloons were filled with water to test for leaks; in this experiment, 11 out of 12 balloons did not leak, for a yield of over 90%. Balloons may still become damaged when they are mounted onto bioreactor attachment hardware, and the assembled system should be checked again for leaks prior to hvCOC fabrication. From each batch, two non-leaky balloons were dissected into their top, middle, and bottom sections. Slices of material were positioned on their cut side and imaged with low-power magnification to get a cross-sectional view (FIG. 12A), from which ImageJ software was used to measure thickness at three locations, and averaged to represent the thickness of that section of that balloon. On average, each slice of material analyzed was 890±270 µm in length. The average standard deviation for the three thickness measurements for each slice was 3.5±1.7 µm. The average thickness of all slices from the two balloons per batch were used to calculate an average thickness, standard deviation and coefficient of variation per batch. Balloon 3 from Batch 3 was eliminated from the data set as it's COV for thickness was more than 50% greater than the average COV for the data set (FIG. 17A). Removing this balloon, the average thickness across all slices of the five remaining balloons is 59±5.0 µm standard deviation with a COV of 8.6%. A one-way ANOVA was performed to compare batches using the average thickness from each slice of each balloon in the batch (n=6 slices for batches 1 and 2, n=3 slices for batch 3); there was no statistical difference between the batches (p=0.07). One-way ANOVA was also performed to compare top, middle, and bottom locations on the balloon across all samples using the average thickness from each slice from the specific region of each balloon (n=5 slices for top, middle, bottom); there was no statistical difference between the locations (p=0.58).

Figure 17B:
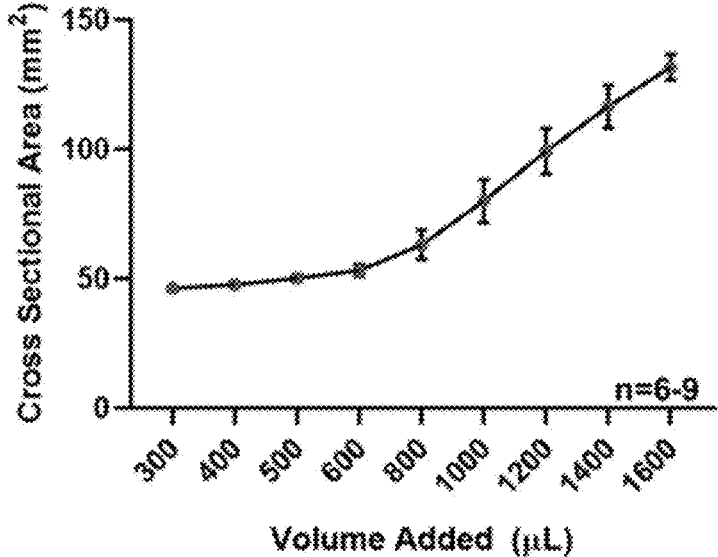
FIG. 17B depicts individual data for cross-sectional area vs. loading volume of 9 balloons (in air). Expansion as a function of loading volume shows small variability across batches and molds.

To ensure that the fabrication protocol was uniform across different batches of material, three different batches of four balloons each were made using a set of four resin casting molds with an unloaded volume of 230 µL. Three out of four of the balloons from each batch were used for testing cross-sectional area as a function of loading volume (300-1600 µL). All data points are plotted in FIG. 17B, showing good consistency among all nine samples based on the average expansion as a function of loading volume.

It is of interest to be able to load the mini-heart chambers and control the amount of strain on the tissue. Ideally, the balloon system allows each tissue to be loaded consistently with a set volume being added to the fluid inlet. To understand the effects of loading volume on internal pressure and how that relates to expansion, a final experiment on balloon consistency across batches was performed. Six balloons across three batches were compared by loading with volumes from 300-500 µL (using smaller volume increments, as this represents the target range for loading biological tissues); for this experiment, a micro-pipettor attached to a stiff, thin piece of tubing was used to accurately deliver liquid to the chamber.

Figure 17C:
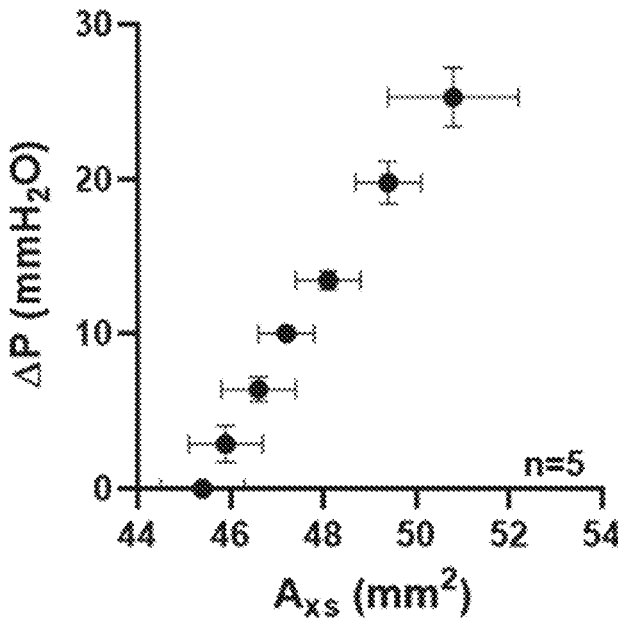
FIG. 17C depicts the response of balloons (n=5) when loaded with 300-500 μL Plot shows $\Delta P$ vs. $A_{xs}$, demonstrating consistency across fabrication batches and molds.

The change in pressure inside the chamber as well as the cross-sectional area were measured at each loading volume. FIG. 17C shows change in pressure vs. cross-sectional area for the 5 intact balloons. The largest coefficient of variation (COV=42%) was seen for the change in pressure for the initial loading step of 25 µL. The large variability here is thought to be a result of the delivery method for small solution volumes, which may have resulted in not all solution making it into the chamber in the first loading step. Subsequent loading steps had COV<15%, which is much more consistent with the structural variability in the balloon fabrication process.

Figure 17D:
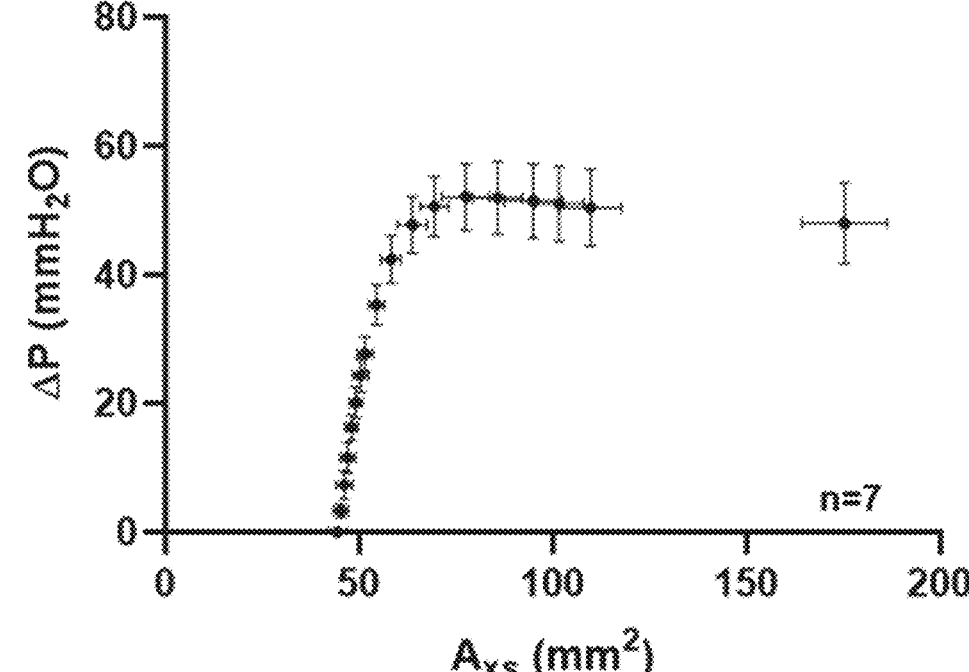
FIG. 17D depicts the response of balloons (n=7) when loaded across a larger range of volumes. Plot shows $\Delta P$ vs. $A_{xs}$. Beginning of curve matches FIG. 17C but change in material behavior is demonstrated at higher loads. All error bars in figure represent the standard deviation.

FIG. 17D repeats the work in FIG. 17C with a new set of balloons (n=7) and explores an extended loading range. At the higher loads, the sigmoidal stress strain curve for the rubber-like material, EcoFlex, alters the response. It is the inventors non-binding hypothesis that at the point where the cross-sectional area expands without an increase in pressure, the balloon material has entered a region strain softening due to overstretching of the membrane, allowing small changes of the inflation pressure to cause the balloon to stretch enough to easily account for the additional liquid. The loading range of 300-500 µL falls within the linear part of the curve.

Based on this mechanical testing, the responses of the balloons across different batches and different molds are consistent and the variation is less than the anticipated variation across biological samples. We have previously reported stroke work for n=25 tissue-only hvCOCs created with the former catheter method to be 5.83±1.27, which correlates to a COV of 109% and exceeds the maximum COV seen for balloon change in pressure as a function of loading volume (max 42%).[10] The ultra-compliant indwelling balloons disclosed herein help to standardize the hvCOC measurement platform across tissue samples and not significantly add to the experimental variability.

Example 6. Multi-Well Array Format

Figure 18A:
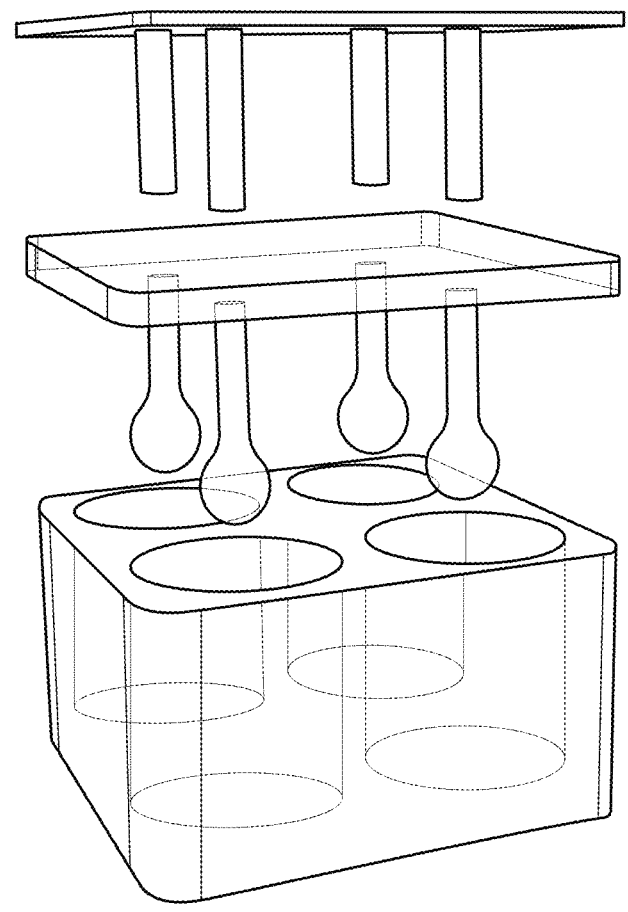
FIG. 18A depicts a method for fitting an array of balloons with rigid cannulas to a 24 well plate. This can be the second step of a two plate transfer scheme for the multi-array format in which a deep well plate is used for tissue formation and a standard 24 well plate is used for culture.
Figure 18B:
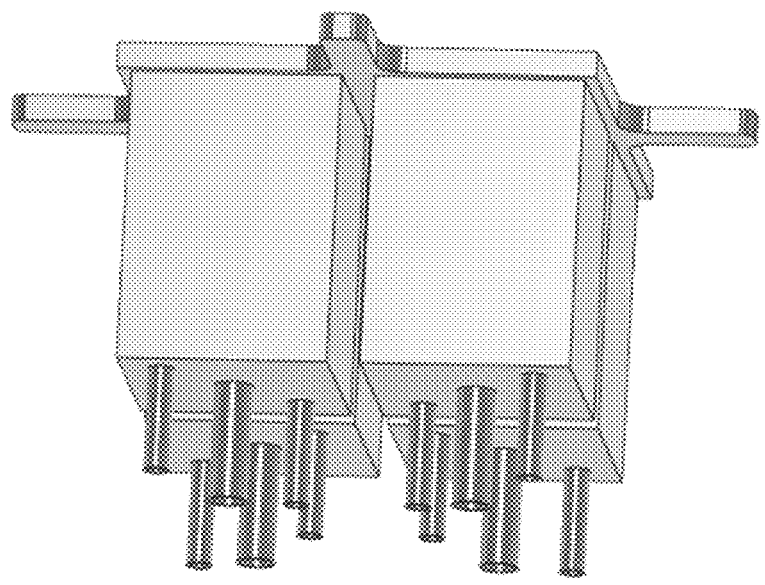
FIG. 18B depicts an insert used to accommodate tissue fabrication in the deep 24 well plate, incorporating electrode ports spread to fit a standard 24 well plate after transfer.

A 2×2 array format fit to a 24 well plate was designed and used to demonstrate the concept of using the balloon in array format for higher throughput versions of the system (FIG. 18A-B). Unlike the fabrication presented above for standard size hvCOCs, the multi-well array format uses a reduced volume balloon, no agarose mold, and a Matrigel/collagen/cell solution that is diluted with culture media. Beating tissues have been fabricated using the system.

REFERENCES

[1] De Clerck, F., Van de Water, A., D'Aubioul, J., Lu, H. R., Van Rossem, K., Hermans, A., & Van Ammel, K. (2002). In vivo measurement of QT prolongation, dispersion and arrhythmogenesis: application to the preclinical cardiovascular safety pharmacology of a new chemical entity. *Fundamental & clinical pharmacology*, 16(2), 125-140.

[2] Milani-Nejad, N., & Janssen, P. M. (2014). Small and large animal models in cardiac contraction research: advantages and disadvantages. *Pharmacology & therapeutics*, 141(3), 235-249.

[3] Magdy, T., Schuldt, A. J., Wu, J. C., Bernstein, D., & Burridge, P. W. (2018). Human induced pluripotent stem cell (hiPSC)-derived cells to assess drug cardiotoxicity: opportunities and problems. *Annual review of pharmacology and toxicology*, 58, 83-103.

[4] Gintant, G., Sager, P. T., & Stockbridge, N. (2016). Evolution of strategies to improve preclinical cardiac safety testing. *Nature reviews Drug discovery*, 15(7), 457.

[5] Shao, Y., Sang, J., & Fu, J. (2015). On human pluripotent stem cell control: The rise of 3D bioengineering and mechanobiology. *Biomaterials*, 52, 26-43.

[6] Wang, J., Chen, A., Lieu, D. K., Karakikes, I., Chen, G., Keung, W., . . . & Li, R. A. (2013). Effect of engineered anisotropy on the susceptibility of human pluripotent stem cell-derived ventricular cardiomyocytes to arrhythmias. *Biomaterials*, 34(35), 8878-8886.

[7] Laverty, H. G., Benson, C., Cartwright, E. J., Cross, M. J., Garland, C., Hammond, T., . . . & Pirmohamed, M. (2011). How can we improve our understanding of cardiovascular safety liabilities to develop safer medicines?. *British journal of pharmacology*, 163(4), 675-693.

[8] Ferri, N., Siegl, P., Corsini, A., Herrmann, J., Lerman, A., & Benghozi, R. (2013). Drug attrition during pre-clinical and clinical development: understanding and managing drug-induced cardiotoxicity. *Pharmacology & therapeutics*, 138(3), 470-484.

[9] Yin, X., Mead, B. E., Safaee, H., Langer, R., Karp, J. M., & Levy, 0. (2016). Engineering stem cell organoids. *Cell stem cell*, 18(1), 25-38.

[10] Li, R. A., Keung, W., Cashman, T. J., Backeris, P. C., Johnson, B. V., Bardot, E. S., . . . & Costa, K. D. (2018). Bioengineering an electro-mechanically functional miniature ventricular heart chamber from human pluripotent stem cells. *Biomaterials*, 163, 116-127.

[11] Zhang, Y. S., Yue, K., Aleman, J., Mollazadeh-Moghaddam, K., Bakht, S. M., Yang, J., . . . & Dokmeci, M. R. (2017). 3D bioprinting for tissue and organ fabrication. *Annals of biomedical engineering*, 45(1), 148-163.

[12] Tsuruyama, S., Matsuura, K., Sakaguchi, K., & Shimizu, T. (2019). Pulsatile tubular cardiac tissues fabricated by wrapping human iPS cells-derived cardiomyocyte sheets. *Regenerative therapy*, 11, 297-305.

[13] Cox, T. R., & Erler, J. T. (2011). Remodeling and homeostasis of the extracellular matrix: implications for fibrotic diseases and cancer. *Disease models & mechanisms*, 4(2), 165-178.

[14] Lee, A., Brun, P. T., Marthelot, J., Balestra, G., Gallaire, F., & Reis, P. M. (2016). Fabrication of slender elastic shells by the coating of curved surfaces. *Nature communications*, 7, 11155.

[15] Colombo, A., Cahill, P. A., & Lally, C. (2008). An analysis of the strain field in biaxial Flexcell membranes for different waveforms and frequencies. *Proceedings of the Institution of Mechanical Engineers, Part H: Journal of Engineering in Medicine*, 222(8), 1235-1245.

[16] Pegan, J. D., Zhang, J., Chu, M., Nguyen, T., Park, S. J., Paul, A., . . . & Khine, M. (2016). Skin-mountable stretch sensor for wearable health monitoring. *Nanoscale*, 8(39), 17295-17303.

[17] Saab, M. A. (2000). Applications of high-pressure balloons in the medical device industry. *Medical Device & Diagnostic Industry Magazine*, 86-94.

[18] Basu, A., Haim-Zada, M., & Domb, A. J. (2016). Biodegradable inflatable balloons for tissue separation. *Biomaterials*, 105, 109-116.

[19] Sun, G., Wei, D., Liu, X., Chen, Y., Li, M., He, D., & Zhong, J. (2013). Novel biodegradable electrospun nanofibrous P (DLLA-CL) balloons for the treatment of vertebral compression fractures. *Nanomedicine: Nanotechnology, Biology and Medicine*, 9(6), 829-838.

[20] Byrne, R. A., Stone, G. W., Ormiston, J., & Kastrati, A. (2017). Coronary balloon angioplasty, stents, and scaffolds. *The Lancet*, 390(10096), 781-792.

[21] Scheller, B., Hehrlein, C., Bocksch, W., Rutsch, W., Haghi, D., Dietz, U., . . . & Speck, U. (2006). Treatment of coronary in-stent restenosis with a paclitaxel-coated balloon catheter. *New England journal of medicine*, 355 (20), 2113-2124.

[22] Lee, K., Lee, S. G., Jang, I., Park, S. H., Yang, D., Seo, I. H., . . . & Jang, Y. H. (2018). Linear Micro-patterned Drug Eluting Balloon (LMDEB) for Enhanced Endovascular Drug Delivery. *Scientific reports*, 8(1), 1-13.

[23] Oberhoff, M., Kunert, W., Herdeg, C., Küttner, A., Kranzhöfer, A., Horch, B., . . . & Karsch, K. P. (2001). Inhibition of smooth muscle cell proliferation after local drug delivery of the antimitotic drug paclitaxel using a porous balloon catheter. *Basic research in cardiology*, 96(3), 275-282.

[24] Stampfl, A., Maier, M., Radykewicz, R., Reitmeir, P., Göttlicher, M., & Niessner, R. (2011). Langendorff heart: a model system to study cardiovascular effects of engineered nanoparticles. *ACS nano*, 5(7), 5345-5353.

[25] Su, Y., Liu, Z., Wang, S., Ghaffari, R., Kim, D. H., Hwang, K. C., . . . & Huang, Y. (2014). Mechanics of stretchable electronics on balloon catheter under extreme deformation. *International Journal of Solids and Structures*, 51(7-8), 1555-1561.

[26] Wang, R., Huang, X., Liu, G., Wang, W., Dong, F., & Li, Z. (2010). Fabrication and characterization of a parylene-based three-dimensional microelectrode array for use in retinal prosthesis. *Journal of Microelectromechanical Systems*, 19(2), 367-374.

[27] Pakazad, S. K., Savov, A., Van de Stolpe, A., & Dekker, R. (2014). A novel stretchable micro-electrode array (SMEA) design for directional stretching of cells. *Journal of Micromechanics and Microengineering*, 24(3), 034003.

[28] Jepsen, M. L., Nielsen, L. H., Boisen, A., Almdal, K., & Dufva, M. (2019). Characterization of thin gelatin hydrogel membranes with balloon properties for dynamic tissue engineering. *Biopolymers*, 110(1), e23241.

EMBODIMENTS

Embodiment 1. A tissue support comprising a fluid-impermeable resilient member having an external surface and defining an enclosed volume;

wherein said external surface of the member is resiliently deformable by cultured tissues formed on the external surface of the member during testing thereof.

Embodiment 2. The tissue support of Embodiment 1, wherein the cultured tissues comprise cardiac cells.

Embodiment 3. The tissue support of Embodiment 2, wherein the cardiac cells are human ventricular-like cardiomyocytes derived from human pluripotent stem cells.

Embodiment 4. The tissue support of Embodiment 1, wherein the cultured tissues are cardiac organoids.

Embodiment 5. The tissue support of Embodiment 4, wherein the cultured tissues are human cardiac ventricular-like organoid chambers.

Embodiment 6. The tissue support of Embodiment 1, wherein the testing is selected from the group consisting of a pressure-volume loop analysis, mechanical stretch measurement, electrophysiological measurement, gene expression analysis at a transcript level, gene expression analysis at a protein level, microstructural analysis using optical microscopy, and microstructural analysis using electron microscopy.

Embodiment 7. The tissue support of Embodiment 6, wherein the electrophysiological measurements include conduction velocity, action potential duration, or conduction pattern.

Embodiment 8. The tissue support of Embodiment 1, wherein the testing is a pressure-volume loop analysis.

Embodiment 9. The tissue support of Embodiment 1, wherein the testing is performed to study the Frank-Starling mechanism of the cultured tissues.

Embodiment 10. The tissue support of Embodiment 1, wherein the testing is performed in the presence of an electric field proximate the support.

Embodiment 11. The tissue support of Embodiment 1, wherein the cultured tissues are stretched for testing by increasing hydrostatic loading of the enclosed volume.

Embodiment 12. The tissue support of Embodiment 1, wherein the resilient deformation of the external surface of the member into the enclosed volume causes a measurable change in the cross sectional area and enclosed volume of the member.

Embodiment 13. The tissue support of Embodiment 1, wherein the fluid impermeable member defines a substantially spherical enclosed volume in an inflated state.

Embodiment 14. The tissue support of Embodiment 1, wherein the fluid impermeable member is formed as a generally spherical balloon in an inflated state.

Embodiment 15. The tissue support of Embodiment 1, wherein the inflation of the fluid impermeable member allows the enclosed volume to assume a predetermined size and shape.

Embodiment 16. The tissue support of Embodiment 1, wherein the fluid impermeable member has a wall of generally consistent thickness, said thickness between a thickness of 40-300 µm, more preferably 40-120 µm, more preferably 40-60 µm.

Embodiment 17. The tissue support of Embodiment 1, wherein the fluid impermeable member further comprises an elongate support portion attachable to a fluid loading port.

Embodiment 18. The tissue support of Embodiment 1, wherein the cross sectional area of the fluid impermeable member increases generally linearly relative to loading volume of solutions between a range of 300 to 600 µL into the enclosed volume.

Embodiment 19. The tissue support of Embodiment 1, wherein the fluid impermeable member is formed by a polymeric material with elastic modulus of 1 kPa-10 MPa, preferably 20 kPa-200 kPa, and more preferably 60 kPa.

Embodiment 20. The tissue support of Embodiment 19, wherein the polymeric material is selected from polydimethylsiloxane, EcoFlex and NuSil polymers.

Embodiment 21. The tissue support of Embodiment 1, wherein the relative stiffness of the fluid resilient member is at least one order of magnitude less than the relative stiffness of the tissue supported thereon.

Embodiment 22. The tissue support of Embodiment 1, the external surface is provided with one or more topological features to guide biophysical interaction between the tissue and the tissue support.

Embodiment 23. The tissue support of Embodiment 22, wherein the topological features are one or more of the group of topological features comprising grooves, ridges, channels, bumps, knobs, dimples, holes, pillars, other protrusions with both rough and smooth finishes.

Embodiment 24. The tissue support of Embodiment 1, wherein the external surface is provided with patterned electrodes.

Embodiment 25. The tissue support of Embodiment 1, wherein the external surface is provided with a stretch sensor.

Embodiment 26. The tissue support of Embodiment 1, wherein the fluid impermeable member is formed by drop casting of a polymeric material on a 3D printed mold.

Embodiment 27. A system for observing properties of cultured tissue during testing analysis thereof, the system comprising:

a fluid impermeable resilient member having an external surface and defining an enclosed volume; and a cultured tissue construct extending about the fluid impermeable member and supported thereon;

wherein said external surface of the member is resiliently deformable by the tissue constructs during testing thereof.

Embodiment 28. The system of Embodiment 27, wherein the cultured tissues comprise cardiac cells.

Embodiment 29. The system of Embodiment 28, wherein the cardiac cells are human ventricular-like cardiomyocytes derived from human pluripotent stem cells.

Embodiment 30. The system of Embodiment 27, wherein the cultured tissues are cardiac organoids.

Embodiment 31. The system of Embodiment 30, wherein the cultured tissues are human cardiac ventricular like organoid chambers.

Embodiment 32. The system of Embodiment 27, wherein the testing is selected from the group consisting of a pressure-volume loop analysis, mechanical stretch measurement, electrophysiological measurement, gene expression analysis at a transcript level, gene expression analysis at a protein level, microstructural analysis using optical microscopy, and microstructural analysis using electron microscopy.

Embodiment 33. The system of Embodiment 32, wherein the electrophysiological measurements include conduction velocity, action potential duration, or conduction pattern.

Embodiment 34. The system of Embodiment 27, wherein the testing is a pressure-volume loop analysis.

Embodiment 35. The system of Embodiment 27, wherein the testing is performed to study the Frank-Starling mechanism of the cultured tissues.

Embodiment 36. The system of Embodiment 27, wherein the testing is performed in the presence of an electric field.

Embodiment 37. The system of Embodiment 27, wherein the cultured tissues are stretched for testing by increasing a hydrostatic loading in the enclosed volume, stretching the cardiac tissue.

Embodiment 38. The system of Embodiment 27, wherein the resilient deformation of the external surface of the member into the enclosed volume causes a measurable change in the cross sectional area and enclosed volume of the member.

Embodiment 39. The system of Embodiment 27, wherein the fluid impermeable member defines a substantially spherical enclosed volume in an inflated state.

Embodiment 40. The system of Embodiment 27, wherein the fluid impermeable member is formed as a generally spherical balloon in an inflated state.

Embodiment 41. The system of Embodiment 27, wherein the inflation of the fluid impermeable member allows the enclosed volume to assume a predetermined size and shape.

Embodiment 42. The system of Embodiment 27, wherein fluid impermeable member has a wall of generally consistent thickness of 40-300 µm, more preferably 40-120 µm, more preferably 40-60 µm.

Embodiment 43. The system of Embodiment 27, wherein fluid impermeable member further comprises an elongate support portion attachable to a fluid loading port.

Embodiment 44. The system of Embodiment 27, wherein the cross sectional area of the fluid impermeable member increases generally linearly relative to loading volume of solutions between a range of 300 to 600 uL into the enclosed volume.

Embodiment 45. The system of Embodiment 27, wherein the fluid impermeable member is formed by a polymeric material with elastic modulus of 1 kPa-10 MPa, preferably 20 kPa-200 kPa, and more preferably 60 kPa.

Embodiment 46. The system of Embodiment 45, wherein the polymeric material is selected from polydimethylsiloxane, EcoFlex and NuSil polymers.

Embodiment 47. The system of Embodiment 27, wherein the relative stiffness of the fluid resilient member is at least one order of magnitude less than the relative stiffness of the tissue supported thereon.

Embodiment 48. The system of Embodiment 27, the external surface is provided with one or more topological features to guide biophysical interaction between the tissue and the balloon.

Embodiment 49. The system of Embodiment 48, wherein the topological features are one or more of the group of topological features comprising grooves, ridges, channels, bumps, knobs, dimples, holes, pillars, other protrusions with both rough and smooth finishes.

Embodiment 50. The system of Embodiment 27, wherein the external surface is provided with patterned electrodes.

Embodiment 51. The system of Embodiment 27, wherein the external surface is provided with a stretch sensor.

Embodiment 52. The system of Embodiment 27, wherein the fluid impermeable member is formed by drop casting of a polymeric material on a 3D printed mold.

Embodiment 53. A method of culturing tissues, comprising the step of:
- a) providing a tissue support comprising a fluid impermeable resilient member having an external surface and defining an enclosed volume; wherein said external surface of the member is resiliently deformable by cultured tissues formed on the external surface of the member during testing thereof;
- b) inflating the fluid impermeable resilient member;
- c) depositing cells onto the fluid impermeable resilient member; and
- d) culturing the cells in a medium.

Embodiment 54. The method of Embodiment 53, further comprises attaching the tissue support on to a fluid loading port via an elongate support portion of the tissue support.

Embodiment 55. The method of Embodiment 53, wherein the method further comprises adding fluid to the fluid impermeable resilient member via the fluid loading port.

Embodiment 56. The method of Embodiment 53, wherein the method further comprises placing the tissue support in a chamber formed in a hydrogel mold in a bioreactor.

Embodiment 57. The method of Embodiment 53, wherein the cells are human ventricular-like cardiomyocytes derived from human pluripotent stem cells.

Embodiment 58. The method of Embodiment 53, wherein the cultured tissues are human cardiac ventricular like organoid chambers.

Embodiment 59. The method of Embodiment 53, wherein the testing is selected from the group consisting of a pressure-volume loop analysis, mechanical stretch measurement, electrophysiological measurement, gene expression analysis at a transcript level, gene expression analysis at a protein level, microstructural analysis using optical microscopy, and microstructural analysis using electron microscopy.

Embodiment 60. The method of Embodiment 59, wherein the electrophysiological measurements including conduction velocity, action potential duration, or conduction pattern.

Embodiment 61. The method of Embodiment 53, wherein the testing is a pressure-volume loop analysis, a testing for studying the Frank-Starling mechanism of the cultured tissues, or a testing performed in the presence of an electric field.

Embodiment 62. The method of Embodiment 53, wherein the resilient deformation of the external surface of the member into the enclosed volume causes a measurable change in the cross sectional area and enclosed volume of the member.

Embodiment 63. The method of Embodiment 53, wherein the fluid impermeable member defines a substantially spherical enclosed volume in an inflated state.

Embodiment 64. The method of Embodiment 53, wherein the fluid impermeable member is formed as a generally spherical balloon in an inflated state.

Embodiment 65. The method of Embodiment 53, wherein the inflation of the fluid impermeable member allows the enclosed volume to assume a predetermined size and shape.

Embodiment 66. A method of fabrication of a tissue support comprising a fluid impermeable resilient member having an external surface and defining an enclosed volume; the method comprises the steps of:
- a) forming a thin film of polymer on a mold;
- b) curing the polymer to form the tissue support; and
- c) removing the tissue support from the mold;
  wherein said support comprises a resilient external surface of the member that is resiliently deformable by cultured tissues formed on the external surface of the member during testing thereof.

Embodiment 67. The method of Embodiment 66, wherein the polymeric material has elastic modulus of 1 kPa-10 MPa, preferably 20 kPa-200 kPa, and more preferably 60 kPa.

Embodiment 68. The method of Embodiment 67, wherein the polymeric material is selected from polydimethylsiloxane, EcoFlex and NuSil polymers.

Embodiment 69. The method of Embodiment 66, wherein the mold comprises a generally spherical portion, and an elongate portion, attachable to the sphere shaped portion.

Embodiment 70. The method of Embodiment 66, wherein the mold has a shape derived from 3D medical imaging techniques.

Embodiment 71. The method of Embodiment 66, wherein the external surface of the mold comprises one or more topological features to guide biophysical interaction between the tissue and the balloon.

Embodiment 72. The method of Embodiment 71, wherein the topological features are one or more of the group of topological features comprising grooves, ridges, channels, bumps, knobs, dimples, holes, pillars, other protrusions with both rough and smooth finishes.

Embodiment 73. The method of Embodiment 66, wherein the mold is formed by 3D printing or milling.

Embodiment 74. The method of Embodiment 66, wherein the mold is dissolvable.

Embodiment 75. The method of Embodiment 66, wherein the thin film of polymer is fabricated on the mold by drop-casting, dip-coating, injection mold, lost-wax casting or soap casting.

Embodiment 76. The method of Embodiment 66, wherein the method is an automated high-throughput process.

Embodiment 77. The method of Embodiment 76, wherein the tissue support comprises a multiwell format.

Embodiment 78. The tissue support of Embodiment 1, wherein the human pluripotent stem cells are induced human pluripotent stem cells.

Embodiment 79. The tissue support of Embodiment 77, wherein the induced pluripotent stem cells are differentiated into cardiomyocytes.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A tissue support comprising a fluid-impermeable resilient member having an external surface and defining an enclosed volume;

wherein the external surface of the fluid-impermeable resilient member is resiliently deformable by cultured tissues formed on the external surface of the fluid-impermeable resilient member during testing thereof, and wherein the fluid-impermeable resilient member is retained in place during the testing.

2. The tissue support of claim 1, wherein the cultured tissues comprise cardiac cells or cardiac organoids.

3. The tissue support of claim 1, wherein the testing is a pressure-volume loop analysis.

4. The tissue support of claim 1, wherein the resilient deformation of the external surface of the fluid-impermeable resilient member into the enclosed volume causes a measurable change in the cross sectional area and enclosed volume of the fluid-impermeable resilient member.

5. The tissue support of claim 1, wherein the fluid-impermeable resilient member defines a substantially spherical enclosed volume in an inflated state.

6. The tissue support of claim 5, wherein the inflation of the fluid-impermeable resilient member allows the enclosed volume to assume a predetermined size and shape.

7. The tissue support of claim 1, wherein the fluid-impermeable resilient member has a wall of generally consistent thickness, the thickness between 40-300 $\mu$m.

8. The tissue support of claim 1, wherein the fluid-impermeable resilient member further comprises an elongate support portion attachable to a fluid loading port.

9. The tissue support of claim 1, wherein the cross sectional area of the fluid-impermeable resilient member increases generally linearly relative to loading volume of solutions between a range of 300 to 600 $\mu$L into the enclosed volume.

US 12,686,852 B2

37

10. The tissue support of claim 1, wherein the fluid-impermeable resilient member is formed by a polymeric material with elastic modulus of 1 k Pa-10 MPa.

11. The tissue support of claim 1, wherein the external surface of the fluid-impermeable resilient member is provided with one or more topological features to guide biophysical interaction between the tissue and the tissue support.

12. A tissue support comprising:
a fluid-impermeable resilient member having an external surface and defining an enclosed volume, and a wall of generally consistent thickness between 40-300 μm;
wherein the external surface of the fluid-impermeable resilient member is resiliently deformable by cultured tissues formed on the external surface of the fluid-impermeable resilient member during testing thereof.

13. A tissue support comprising:
a fluid-impermeable resilient member having an external surface and defining an enclosed volume having a loading volume between a range of 300 to 600 μL;
wherein the external surface of the fluid-impermeable resilient member is resiliently deformable by cultured tissues formed on the external surface of the fluid-impermeable resilient member during testing thereof.

* * * * *

38